(12) United States Patent
McGregor et al.

(10) Patent No.: US 10,874,546 B2
(45) Date of Patent: Dec. 29, 2020

(54) CONVECTIVE SYSTEM WITH HOSE MANIFOLD

(71) Applicant: 3M INNOVATIVE PROPERTIES COMPANY, St. Paul, MN (US)

(72) Inventors: Andrew J. McGregor, Minneapolis, MN (US); James E. Nash, Bloomington, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 298 days.

(21) Appl. No.: 15/535,566

(22) PCT Filed: Dec. 23, 2015

(86) PCT No.: PCT/US2015/000214
§ 371 (c)(1),
(2) Date: Jun. 13, 2017

(87) PCT Pub. No.: WO2016/105487
PCT Pub. Date: Jun. 30, 2016

(65) Prior Publication Data
US 2017/0360599 A1    Dec. 21, 2017

Related U.S. Application Data

(60) Provisional application No. 62/131,551, filed on Mar. 11, 2015, provisional application No. 62/096,133, filed on Dec. 23, 2014.

(51) Int. Cl.
*A61F 7/00* (2006.01)
*A61F 7/02* (2006.01)
(Continued)

(52) U.S. Cl.
CPC ............... *A61F 7/02* (2013.01); *F16L 33/00* (2013.01); *A61B 90/50* (2016.02);
(Continued)

(58) Field of Classification Search
CPC ............... A61F 7/02; A61F 2007/0091; A61F 2007/006; A61F 2007/0064
See application file for complete search history.

(56) References Cited

U.S. PATENT DOCUMENTS 2,093,834 A * 9/1937 Gaugler ................. F25D 15/00
4/536
4,979,518 A   12/1990 Itoh
(Continued)

FOREIGN PATENT DOCUMENTS

CA    2140753    2/1994
DE    9319969    4/1994
(Continued)

OTHER PUBLICATIONS

International Search Report for PCT International Application No. PCT/US2015/000214, dated Apr. 14, 2016, 5pgs.

*Primary Examiner* — Linda C Dvorak
*Assistant Examiner* — Yasamin Ekrami

(57) ABSTRACT

At least some aspects of the present disclosure feature a convective system including an inflatable convective device and a manifold. The inflatable convective device has a pneumatic structure and two openings into the pneumatic structure. The hose manifold includes a hose connector configured to connect to a hose, two outlet connectors configured to connect to the two openings respectively, where the hose connector and the two output connectors are in fluid connection.

15 Claims, 21 Drawing Sheets

(51) Int. Cl.
*F16L 33/00* (2006.01)
*A61B 90/50* (2016.01)

(52) U.S. Cl.
CPC . *A61F 2007/006* (2013.01); *A61F 2007/0064* (2013.01); *A61F 2007/0091* (2013.01)

(56) References Cited

U.S. PATENT DOCUMENTS

| | | | |
|---|---|---|---|
| 5,062,424 A * | 11/1991 | Hooker | A41D 13/0053 128/897 |
| 5,125,238 A | 6/1992 | Ragan | |
| 5,300,100 A | 4/1994 | Hickle | |
| 5,304,213 A * | 4/1994 | Berke | A47G 9/0215 607/104 |
| 5,443,488 A | 8/1995 | Namenye | |
| 5,514,169 A | 5/1996 | Dickerhoff | |
| 5,824,025 A * | 10/1998 | Augustine | A61F 7/00 607/107 |
| 6,679,432 B1 * | 1/2004 | Arnold | A61F 7/0097 128/202.22 |
| 2002/0100121 A1 * | 8/2002 | Kocurek | A47G 9/0215 5/482 |
| 2003/0036786 A1 | 2/2003 | Duren | |
| 2003/0195596 A1 * | 10/2003 | Augustine | A61F 7/00 607/104 |
| 2005/0107854 A1 * | 5/2005 | Gammons | A61F 7/0097 607/104 |
| 2005/0107856 A1 | 5/2005 | Gammons | |
| 2005/0165400 A1 | 7/2005 | Fernandez | |
| 2006/0174392 A1 * | 8/2006 | Farnworth | A41D 13/0025 2/102 |
| 2006/0184216 A1 * | 8/2006 | Van Duren | A61F 7/0097 607/104 |
| 2008/0077209 A1 * | 3/2008 | Vardanega | A61F 7/0097 607/107 |
| 2010/0076530 A1 * | 3/2010 | Oliver | A62B 17/005 607/104 |
| 2011/0095523 A1 * | 4/2011 | Rose | A62B 17/005 285/122.1 |
| 2011/0176273 A1 * | 7/2011 | Olsen | G06F 1/20 361/679.47 |
| 2015/0335470 A1 * | 11/2015 | Panser | A41D 13/0051 607/107 |

FOREIGN PATENT DOCUMENTS

| | | |
|---|---|---|
| DE | 9416787 | 12/1994 |
| EP | 0659374 | 6/2000 |
| EP | 2474243 | 7/2012 |
| JP | 51-156523 | 12/1976 |
| WO | WO 9520371 | 8/1995 |
| WO | WO 2006101626 | 9/2006 |

* cited by examiner

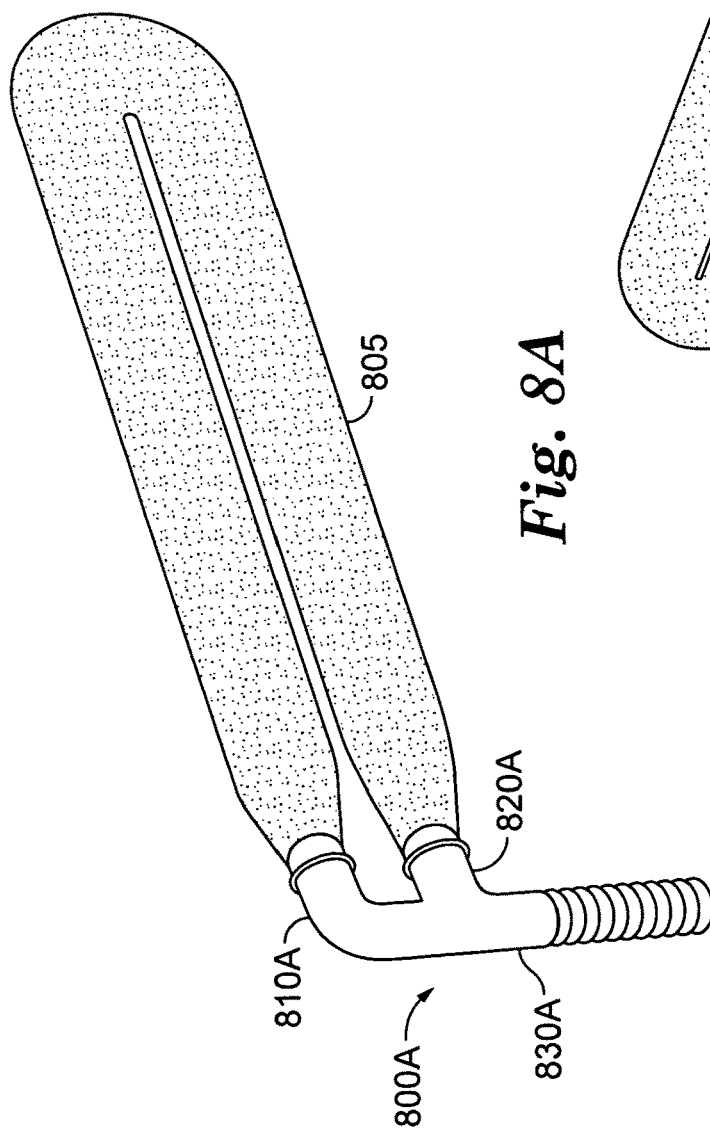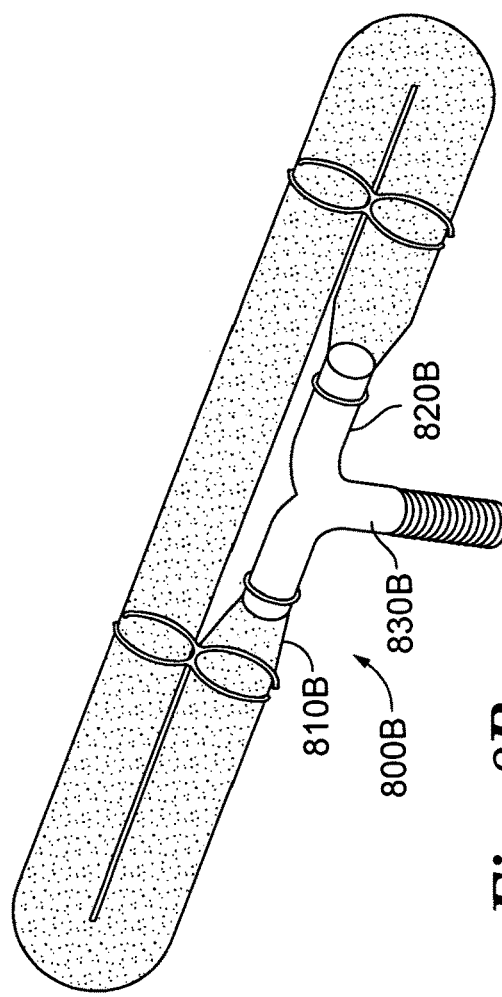

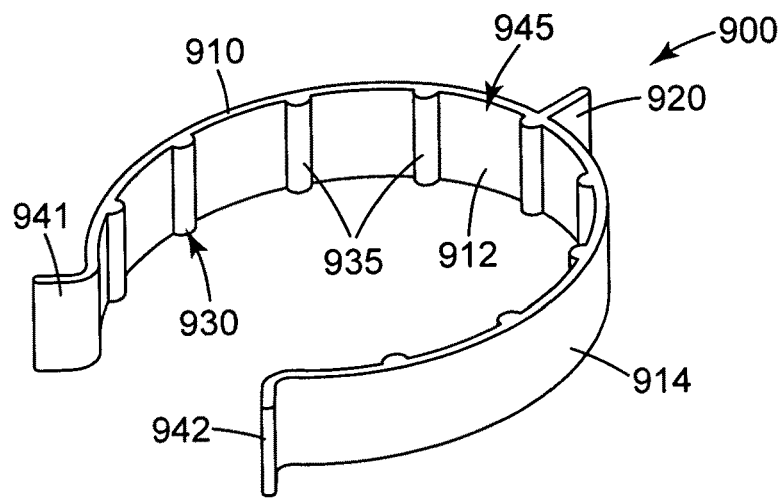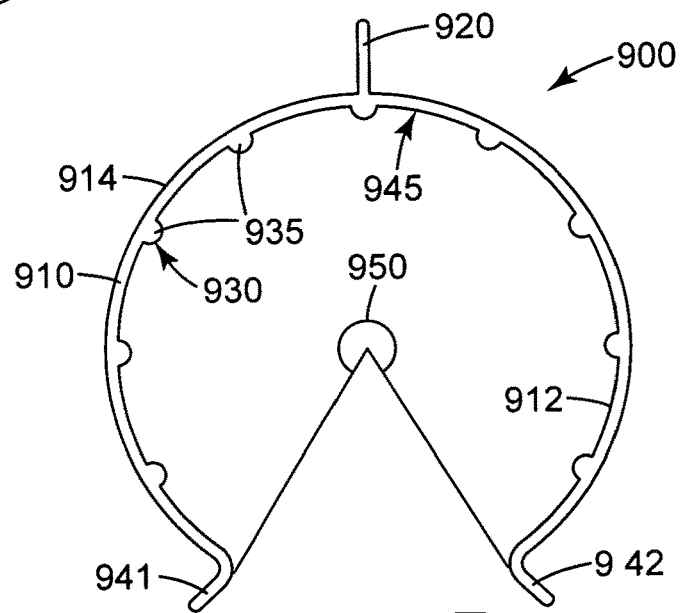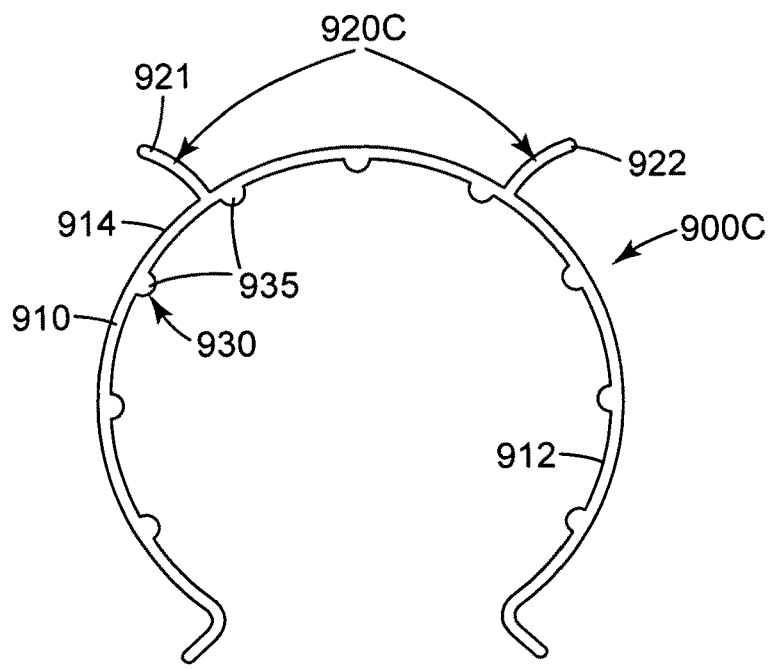

CONVECTIVE SYSTEM WITH HOSE MANIFOLD

CROSS REFERENCE TO RELATED APPLICATIONS

This application is a national stage filing under 35 U.S.C. 371 of PCT/US2015/000214, filed Dec. 23, 2015, which claims the benefit of U.S. Provisional Applications Nos. 62/096,133, filed Dec. 23, 2014, and 62/131,551, filed Mar. 11, 2015, the disclosures of which are incorporated by reference in its/their entirety herein.

TECHNICAL FIELD

The present disclosure is related to convective devices and components to be used in a convective system for warming or cooling.

SUMMARY

At least some aspects of the present disclosure feature a convective system, comprising: an inflatable convective device having a pneumatic structure and two openings into the pneumatic structure, wherein at least part of the convective device is air permeable; and a hose manifold comprising: a hose connector configured to connect to a hose, two outlet connectors configured to connect to the two openings respectively, wherein the hose connector and the two output connectors are in fluid connection.

BRIEF DESCRIPTION OF DRAWINGS

The accompanying drawings are incorporated in and constitute a part of this specification and, together with the description, explain the advantages and principles of the invention. In the drawings.

FIGS. 8A-8G illustrate some examples of hose manifolds;

FIG. 9A illustrates a perspective view of one embodiment of a hose clamp; and FIG. 9B illustrates a side view of the hose clamp illustrated in FIG. 9A;

FIG. 9C illustrates a side view of another embodiment of a hose clamp;

Figure 1A:
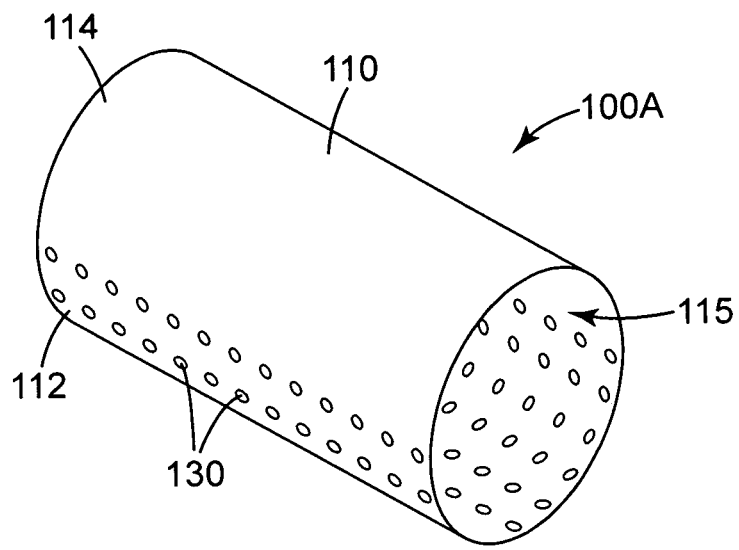
FIG. 1A illustrates a close-up view of one embodiment of a tubular convective device.

In the drawings, like reference numerals indicate like elements. While the above-identified drawing, which may not be drawn to scale, sets forth various embodiments of the present disclosure, other embodiments are also contemplated, as noted in the Detailed Description. In all cases, this disclosure describes the presently disclosed disclosure by way of representation of exemplary embodiments and not by express limitations. It should be understood that numerous other modifications and embodiments can be devised by those skilled in the art, which fall within the scope and spirit of this disclosure.

DETAILED DESCRIPTION

Unless otherwise indicated, all numbers expressing feature sizes, amounts, and physical properties used in the specification and claims are to be understood as being modified in all instances by the term "about." Accordingly, unless indicated to the contrary, the numerical parameters set forth in the foregoing specification and attached claims are approximations that can vary depending upon the desired properties sought to be obtained by those skilled in the art utilizing the teachings disclosed herein. The use of numerical ranges by endpoints includes all numbers within that range (e.g. 1 to 5 includes 1, 1.5, 2, 2.75, 3, 3.80, 4, and 5) and any range within that range.

As used in this specification and the appended claims, the singular forms "a," "an," and "the" encompass embodiments having plural referents, unless the content clearly dictates otherwise. As used in this specification and the appended claims, the term "or" is generally employed in its sense including "and/or" unless the content clearly dictates otherwise.

Convective devices generally refer to a device distributing matter in gas state. For example, convective devices can receive a stream of pressurized, warmed air, inflate in response to the pressurized air, distribute the warmed air within a pneumatic structure, and emit the warmed air onto a body to accomplish such objectives as increasing comfort, reducing shivering, and treating or preventing hypothermia. In some embodiments, a convective device is a tubular convective device made from blown film. In such embodiments, the convective device does not use seals to form the pneumatic structure. In some cases, the convective device includes a homogeneous material to form the pneumatic structure. In some cases, at least part of the convective device has apertures of various shapes allowing pressured fluid to go through. In some embodiments, multiple tubular convective devices with or without tear perforations are formed in a roll.

In some embodiments, a convective device has a pneumatic structure that is formed by two layers, each layer including one or more sheets, and at least one of the layers is air permeable that allows air distribution. As used herein, "inflatable" refers to a structure which increases in volume when air or other gas is supplied at a pressure greater than atmospheric pressure to the interior of the structure. Typically these structures inflate at relatively low pressures such as pressures less than 100 mmHg, preferably at pressures less than 50 mmHg, more preferably at pressures less than 25 mmHg. In some cases, the volume of the inflatable section can increase by greater than 100%. Typically, the pneumatic structure is kinked or pinched off proximate to the bending area when the two portions are bent. In some cases, the convective device further includes an air-guide device in the pneumatic structure adapted to direct inflating medium to reduce pressure drop of the inflating medium at the bending area. As used herein, "in" is used to describe a spatial relationship of generally in the structure including at the edge of the structure. For example, the convective device can include the air-guide device to help form one or more crease(s) when it is inflated, proximate to the air-guide device.

At least some embodiments of the present disclosure direct to a convective system including a convective device and a fixation element that can be used to facilitate placement of the convective device and/or facilitate form management of the convective device. For example, a fixation element having two ring elements can be used to hold two parts of a tubular convective device next to each other forming a blanket. As another example, a fixation element having an attachment device can be used to attach a convective device to a fixture, such as an operating (OR) bed, a hospital bed, an arm rest, or the like.

At least some embodiments of the present disclosure direct to a convective system including a convective device and a hose manifold to connect one hose end to more than one openings of the convective device. In some cases, the hose manifold can be used to connect two ends of a tubular convective device and thereby facilitate shape management. In some cases, the hose manifold provides more than one inputs of pressured inflating medium to allow uniform distribution of the inflating medium. In some cases of distributing heated air, a convective device with two openings connecting with a hose manifold can have a generally uniformed heat distribution.

At least some embodiments of the present disclosure direct to a hose clamp designed to be used with a convective device and a hose to improve air-tight connection and prevent slipping. In some embodiments, the hose clamp includes an encircling element matching the diameter of the hose and a grabbing component to facilitate user operation. In some cases, the hose clamp includes an engaging component disposed on the inner surface of the encircling element to improve gripping power of the hose clamp. The engaging component can include, for example, a plurality of engaging elements, bumps, raise-ups, or the like. In some implementations, the engaging elements are disposed in a pattern on the inner surface of the encircling element. In some cases, at least some of the engaging elements are disposed proximate to one end or both ends of the encircling element.

At least some embodiments of the present disclosure direct to a nozzle configuration designed to be used with a convective device to prevent slip and/or facilitate insertion into the convective device and a hose connecting to an inflation medium source. In some cases, the nozzle includes a hindrance device configured to prevent over insertion. In some cases, the nozzle has a piercing device configured to allow ease of use of the nozzle with the convective device.

FIG. 1A illustrates a close-up view of one embodiment of a tubular convective device 100A. The tubular convective device 100A includes a blown film 110 forming a tube 115 when the blown film is inflated. The blown film 110 has a first portion 112 and a second portion 114, where the two portions are separated longitudinally. In some cases, a plurality of apertures 130 are disposed only on the first portion 112 of the blown film 110. In some other cases, a plurality of apertures 130 are disposed both on the first portion 112 and the second portion 114. The blown film 110 can be made from suitable flexible polymer materials, for example, polyethylene, polyester, polypropylene (PP), high-density polyethylene (HDPE), polyethylene terephthalate (PET), polyamide (PA), or the like. The blown film 110 is typically made from a homogeneous material.

In some embodiments, the plurality of apertures 130 cover at least 10% of surface area of the blow film 110. In some cases, the plurality of apertures 130 cover at least 20% of surface area of the blow film 110. In some cases, the plurality of apertures 130 cover at least 30% of surface area of the blow film 110. Aperture density can vary depending on the size of the aperture and the pressure of inflating medium going into the tubular convective device 100A. It is possible to have the film micro perforated or have large holes. The density of apertures can be associated with the diameter of the tubular convective device 100A. In some cases, the apertures are disposed in a way such that a defused stream of air are provided to allow convective heat to transfer while minimizing impingement of the air stream on the body. The rate of heat transfer is determined by the air velocity and area of contact with the apertures. In some configurations, the diameter of the tubular conductive device increases, the percent of perforated surface area of the blown film decreases. In some embodiments, each of the plurality of apertures 130 has a same size and same geometry shape. In some cases, the plurality of apertures 130 can include apertures of different sizes. For example, the plurality of apertures 130 can have apertures of smaller sizes in the first portion of the tubular convective device and apertures of bigger sizes in the second portion of the tubular convective device. In some cases, the plurality of apertures 130 can have various shapes, for example, round, rectangular, oval, triangle, or the like.

In some embodiments, the first portion 112 and the second portion 114 are each a half portion. In some cases, the plurality of apertures 130 are only disposed on the first portion 112 of the blown film 110. In some other cases, the plurality of apertures 130 are disposed on both the first portion 112 and the second portion 114 of the blown film 110. In yet some other cases, the plurality of apertures are disposed on the second portion 114 of the blown film. In some implementations, the tubular convective device 100A can have apertures of different densities at different parts, for examples, lower density apertures closer to the opening and higher density apertures farther from the opening.

Figure 1B:
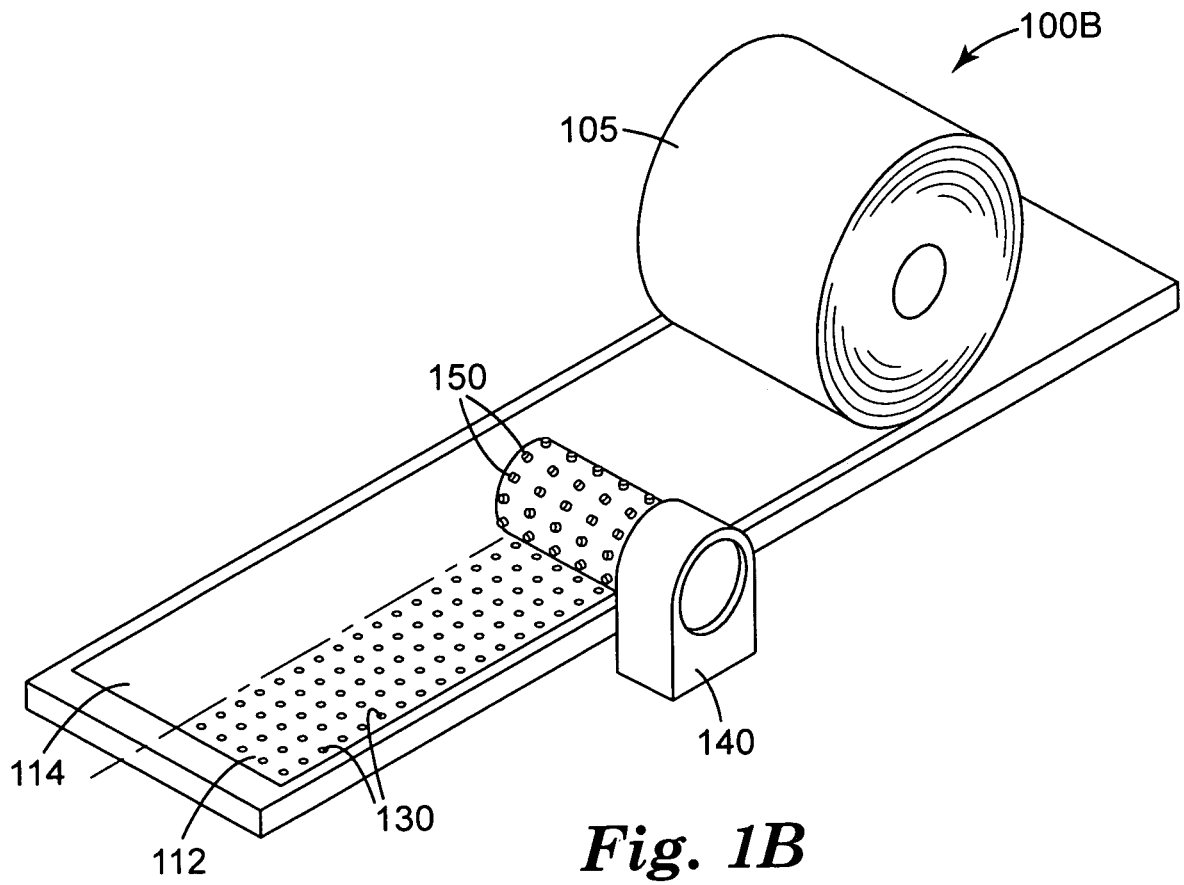
FIG. 1B illustrates one embodiment of a convective system.

FIG. 1B illustrates one embodiment of a convective system 100B having tubular convective devices 105 in a roll. In the embodiment illustrated, the convective system 100B includes a perforation device 140. The perforation device 140 has a plurality of pins 150 to punch apertures on to a series of connected convective devices 105. In some cases, the perforation device 140 can have a pin density in the range of 1-20 per inch$^2$ (1550-31000 per m$^2$). In some cases, the convective devices 105 have existing apertures such that the perforation device 140 is not needed. In some cases, each of the two adjacent convective devices 105 have a separation perforation between adjacent convective devices 105. In some other cases, no separation perforation exists between adjacent convective devices 105, and each convective device 105 is cut when it is to be used. In such cases, the convective system 100B may include a cutter and/or a measurement device for length determination. In some configurations, the tubular convective device can be cut to length, folded and packaged as well.

Figure 2A:
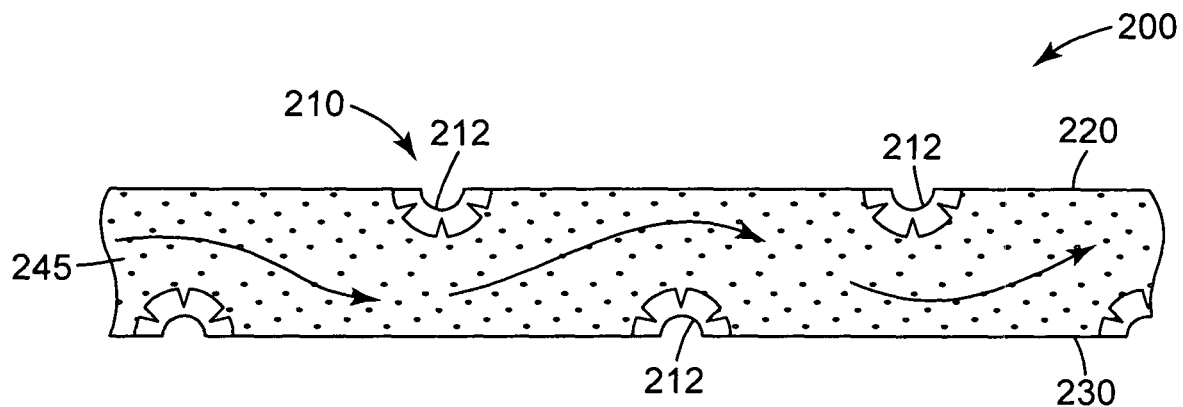
FIG. 2A illustrates one example of a convective device.
Figure 2B:
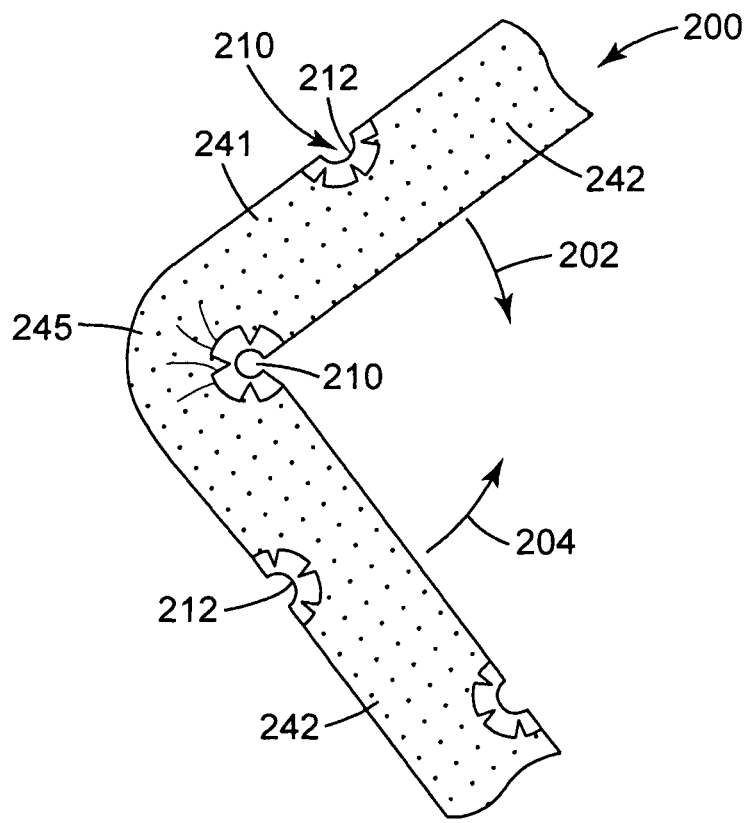
FIG. 2B illustrates the convective device illustrated in FIG. 2A bent at one of the air-guide devices.

FIG. 2A illustrates one example of a convective device 200. The convective device has a first edge 220, a second edge 230, an inflatable channel 245, and an air-guide device 210 configured to direct flow of inflating medium when the convective device is inflated and bent. In some cases, the air-guide device 210 includes a plurality of air-guide elements 212. In some implementations, the air-guide device 210 is disposed proximate to the first edge 220 and/or the second edge 230. In some cases, the air-guide elements 212 are disposed proximate one of the edges (220, 230) in a pattern. In some cases, the air-guide elements 212 disposed proximate to an edge (220 or 230) are disposed in equal spacing. FIG. 2B illustrates the convective device 200 bent proximate to one of the air-guide elements 212, where the convective device 200 is separated into a first portion 241 and a second portion 242 at the bending location. For example, the first portion 241 is bent along the direction 202 and the second portion 242 is bent along the direction 204. In some cases, the air-guide device 210 is disposed proximate to the inflatable channel 245 connecting the first portion 241 and the second portion 242 but not disposed on the edge. In some cases, the air-guide device 210 and the air-guide element 212 is configured to facilitate forming creases at the edge of the air-guide device 210 when the convective device 210 is inflated is bent. In some cases, an air-guide element 210 including a guiding seal extending from an edge of the tubular convective device toward the tube structure.

Figure 3A:
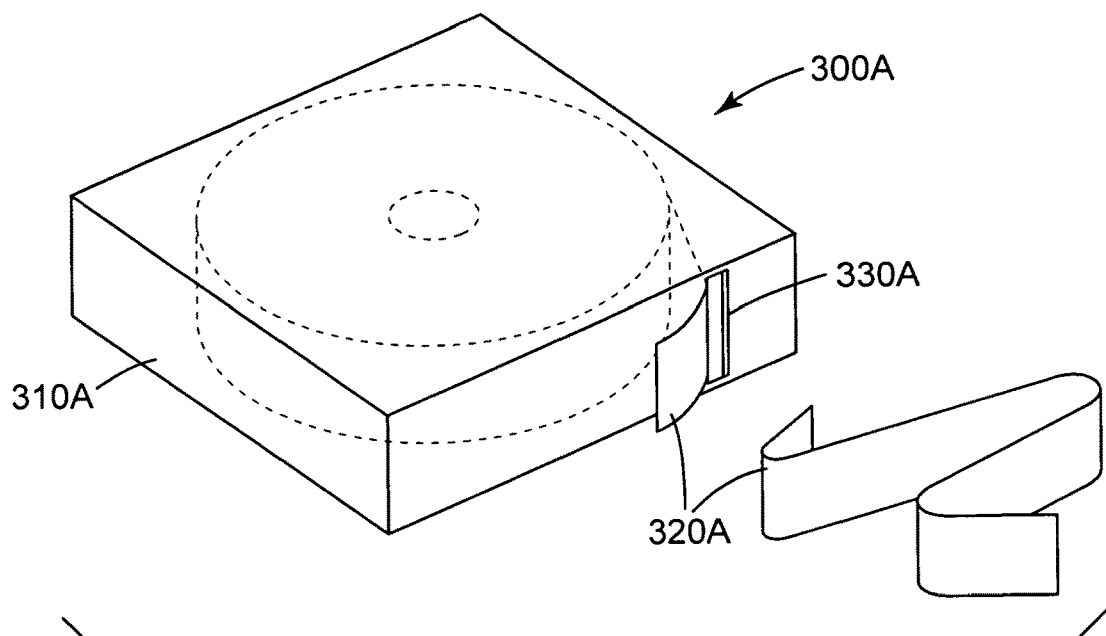
FIGS. 3A and 3B illustrate examples of convective systems.
Figure 3B:
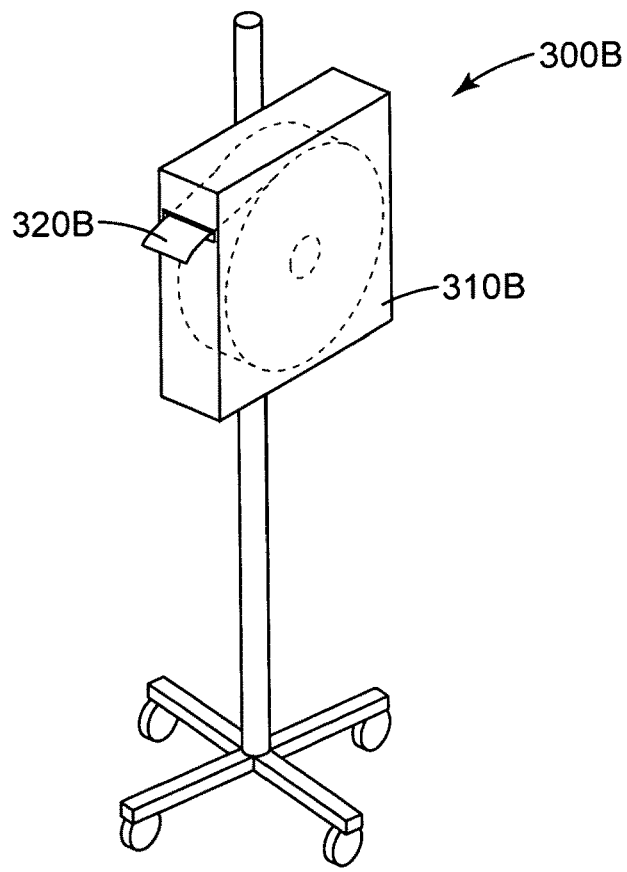

FIGS. 3A and 3B illustrate some examples of convective systems. FIG. 3A illustrates a convective system 300A having a dispenser 310A and a roll of convective devices 320A. The convective device can use any configuration of the tubular convective devices described in the present disclosure. In some cases, the convective system 300A includes a cutting device 330A. In the example illustrated, the cutting device 330A is attached to the dispenser 310A. FIG. 3B illustrates another example of a convective system 300B having a dispenser 310B and a roll of convective devices 320B. The dispenser 310B is in a roller, which allow it to be moved around easily.

Figure 3C:
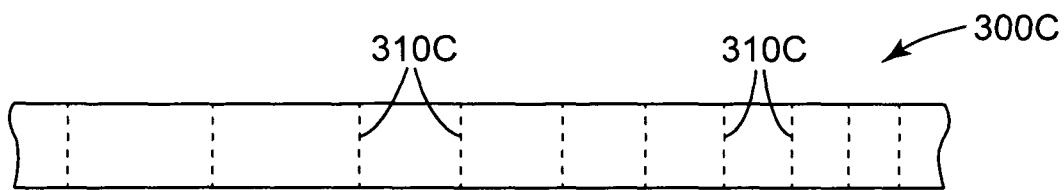
FIGS. 3C-3F illustrate some examples of a bundle of convective devices.

FIGS. 3C-3F illustrate some examples of a bundle of convective devices that are connected. FIG. 3C illustrates a bundle of convective devices 300C, where two adjacent convective devices have a line of weakness 310C in between. The line of weakness 310C allows the convective device to be separated from the bundle 300C. In some cases, each of the convective device in the bundle 300C has the same length. In some other cases, the convective devices in the bundle 300C may have various length.

Figure 3D:
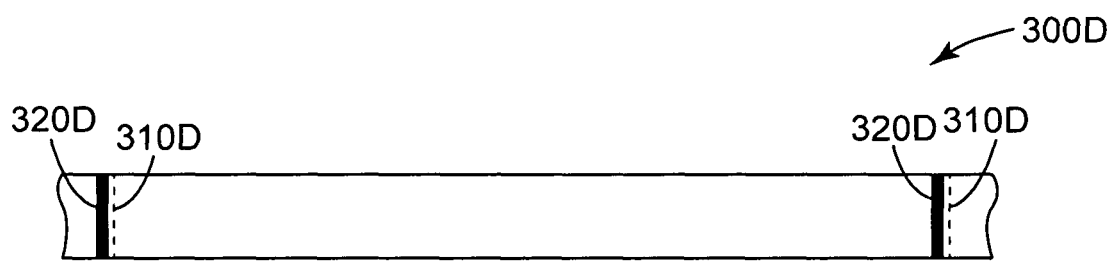

FIG. 3D illustrates a bundle of convective devices 300D, where two adjacent convective devices have a line of weakness 310D and a close seal 320D in between. In the example illustrated, the close seal 320D is disposed proximate to the line of weakness 310D.

Figure 3E:
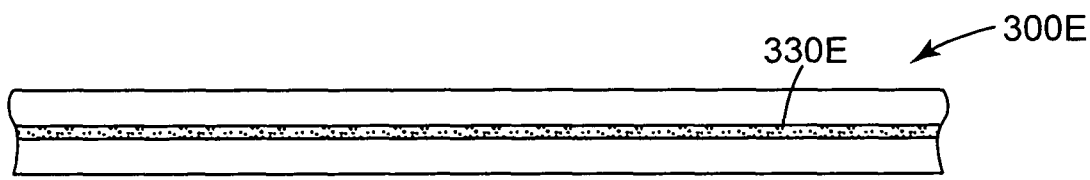
Figure 3F:
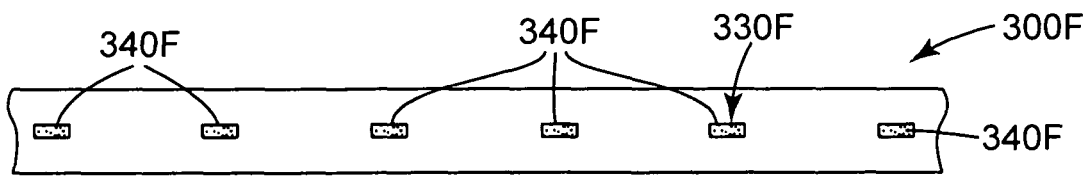

FIG. 3E illustrates a bundle of convective devices 300E with an attachment device 330E. In the example illustrated, the attachment device 330E includes an adhesive strip running longitudinally across the bundle 300E. In some cases, the attachment device 330E is disposed proximate to the middle of the bundle 300E. In some other cases, the attachment device 330E may include two or more adhesive strips. FIG. 3F illustrates a bundle of convective devices 300F with an attachment device 330F. In the example illustrated, the attachment device 330F includes a plurality of adhesive segments 340F disposed in a pattern. In some cases, the plurality of adhesive segments 340F are disposed in a generally equal spacing longitudinally. In some cases, the plurality of adhesive segments 340F are disposed with different distances between adjacent segments.

Figure 4A:
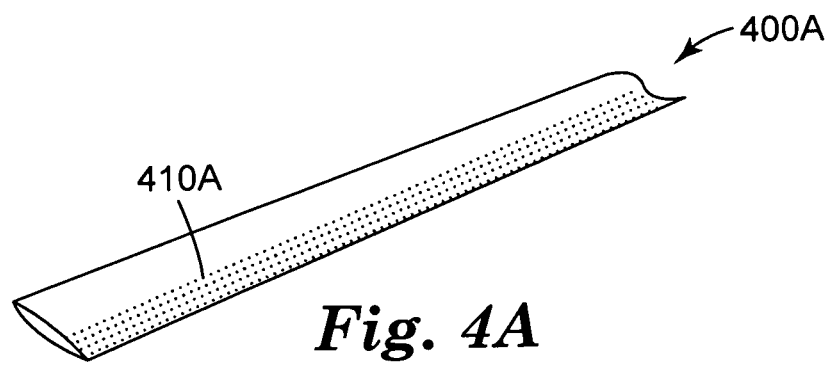
FIGS. 4A-4D illustrate some examples of convective devices.
Figure 4B:
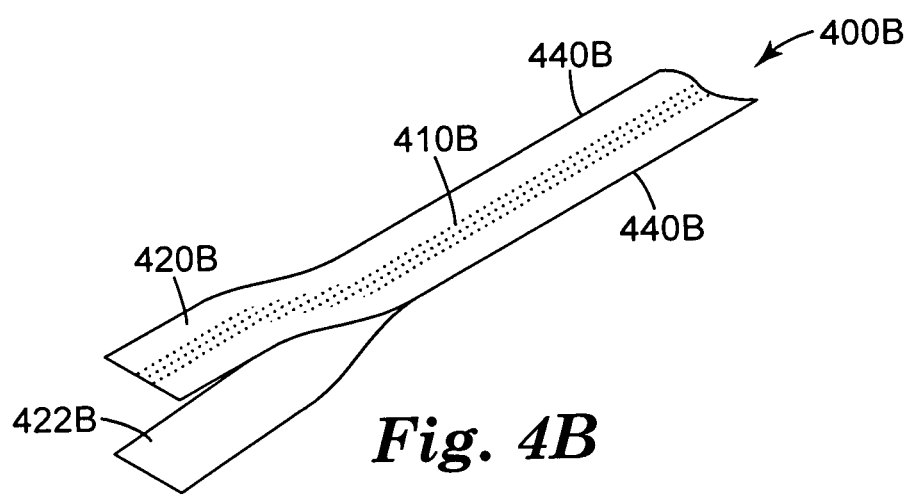
Figure 4C:
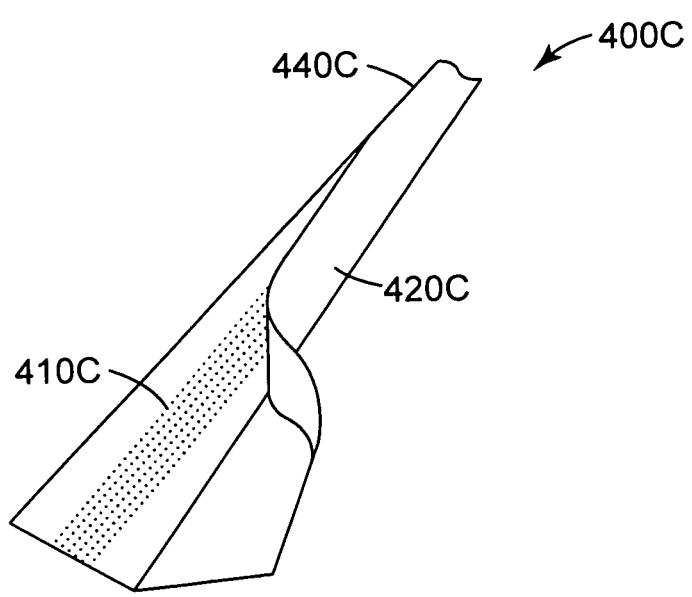

FIGS. 4A-4D illustrate some examples of convective devices. FIG. 4A illustrates a convective device 400A made from blown film, where there are no seals at the longitudinal edges. A plurality of apertures 410A are disposed on a portion or the entire body of the convective device 400A. FIG. 4B illustrates a convective device 400B including two layers 420B and 422B, and the two layers 420B and 422B are sealed at longitudinal edges 440B to form a pneumatic structure. In some cases, one layer 420B includes a plurality of apertures 410B, where the apertures 410B can be disposed before or after the two layers are sealed. In some other cases, one or both layers include apertures or air permeable material. FIG. 4C illustrates a convective device 400C includes one layer 420C that is sealed at its longitudinal edge 440C. In some cases, a plurality of apertures 410C are disposed on a portion or the entire body of the convective device 400C. Typically, the one or more layers of the convective device are made from flexible materials.

Figure 4D:
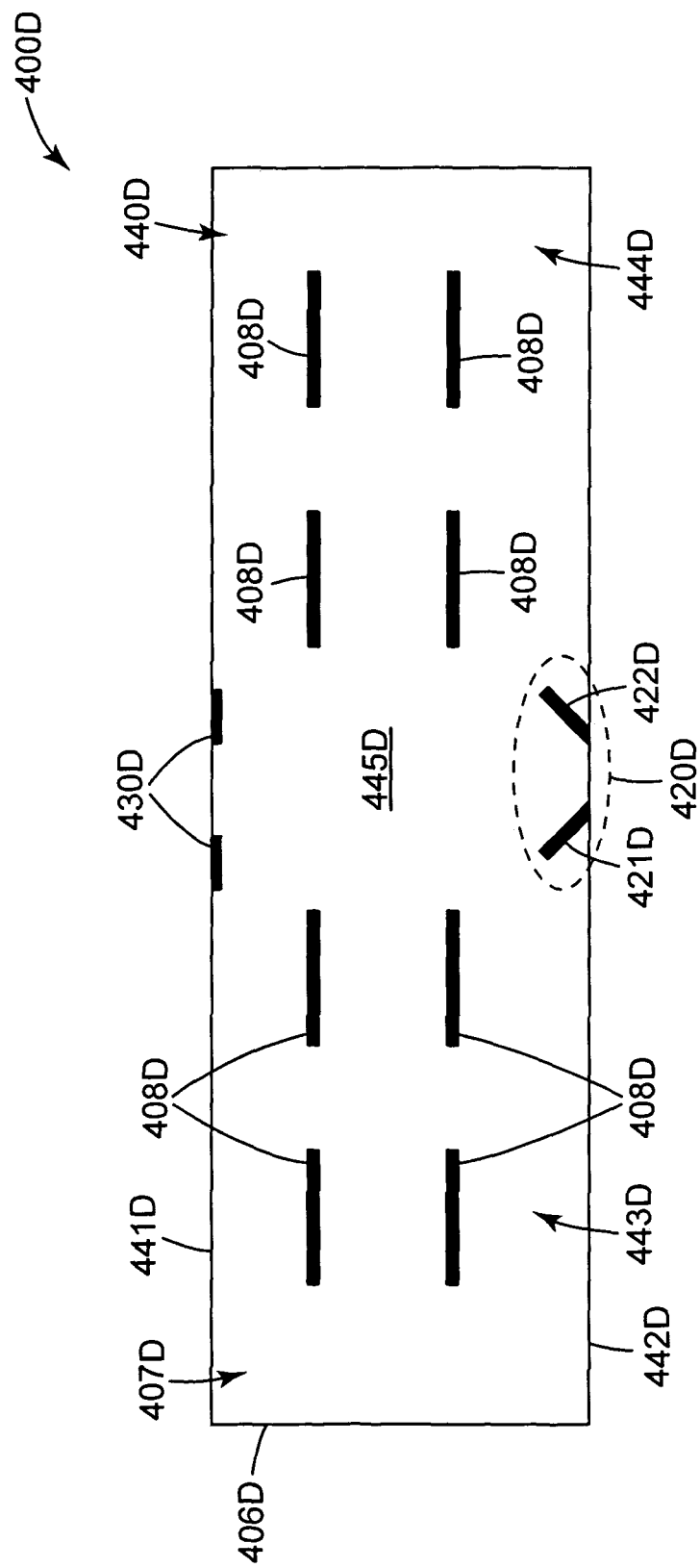

FIG. 4D is a top plane view of one embodiment of a convective device 400D having more than one inflatable channels. In this embodiment, the convective device 400D has a flexible first layer 407D, a flexible second layer (not visible in this view), and two openings 430D. In some cases, the flexible first layer 407D has air permeable surface. The flexible second layer joining the first layer by a seal 406D around a common periphery to form a pneumatic structure 440D, where the pneumatic structure 440D has a first edge 441D and an opposing second edge 442D. The pneumatic structure 440D has a first portion 443D, a second portion 444D, and an inflatable channel 445D connecting the first portion 443D and the second portion 444D, where the first portion and the second portion are generally extending along a same line, for example. The inflatable channel 445D can be formed, for example, by seals 408D. In some cases, the convective device 400D is an inflatable upper body blanket suitable to cover the upper body of a person with arms extending in a clinical position in its original configuration.

In some embodiments, the convective device 400D includes at least one opening 430D into the pneumatic structure 440D. The opening 430D can be in any form that allows an inflating medium source (not illustrated) to connect and provide inflating medium to inflate the pneumatic structure 440D, for example, a sleeve opening at the edge as illustrated in FIG. 4D. As other examples, the opening 430D can include one or more inlet ports, cuffs, ports with stiff collars, sleeve openings at the edge, or the like. In one embodiment, the two openings 430D can connect a hose manifold that have two outlet connectors and one hose connector configured to connect to the inflating medium source, which is described in details below.

In some embodiments, the convective device 400D includes an air-guide device 420D. In some cases, the air-guide device 420D is disposed proximate to the second edge 442D of the pneumatic structure 440D and between the first portion 443D and the second portion 444D, which is adapted to direct flow of inflating medium between the two portions, especially when the first portion 443D and/or the second portion 444D are bent. In some cases, the air-guide device 420D is disposed between the first portion 443D and the second portion 444D. In some cases, the air-guide device 420D is configured to facilitate forming creases at the edge of the air-guide device when the configurable convective device 400D is inflated and at least one of the first portion and the second portion are rearranged such that the inflatable channel 445D is bent.

In some cases, the air-guide device 420D is disposed at a center portion of the pneumatic structure that has a starting point at a distance of ¼ of the width from one end and an ending point at a distance of ¼ of the width from the other end. In some cases, the air-guide device 420D is disposed at a center portion of the pneumatic structure that has a starting point at a distance of ⅖ of the width from the one end and an ending point at a distance of ⅖ of the width from the other end. In some cases, the air-guide device 420D is disposed at the portion of the inflatable channel 445D that is closer to the second edge 442D and farther from the first edge 441D. In some embodiments, the air-guide device 420D comprises a guiding seal extending from the second edge 442D and toward the pneumatic structure 440D. In the embodiment as illustrated, the air-guide device 420D comprises two guiding seals 421D and 422D, each guiding seal extending from the second edge 442D and toward the pneumatic structure 440D. In some cases, the two guiding seals (421D, 422D) are directed to a different portion (the first portion 443D or the second portion 444D) of the pneumatic structure 440D. In some cases, the two guiding seals (421D, 422D) are generally perpendicular with each other.

In some embodiments, each layer of a convective device may include one or more sheets of materials. In some implementations, a layer of a convective device may include an underside sheet formed from a flexible, fibrous, preferably non-woven structure composed of polymeric materials capable of bonding to an upper side sheet of a heat-sealable polymeric material. For example, the underside sheet may be a non-woven, hydroentangled polyester material and the upper side layer may include a polyolefin such as a polypropylene film which is extrusion-coated, thermally laminated, or adhesively laminated onto the polyester layer. Alternatively, the underside sheet may comprise a non-woven, paper-based material to which the upper side layer, including either a polyethylene, polyester, or polypropylene film, has been glue laminated. In one embodiment, the upper side and underside sheets can be made with a stratum of absorbent tissue paper prelaminated with a layer of heat-sealable plastic. In some cases, both the first layer and the second layer can include a same polymer material.

In some embodiments, a first layer includes the upper side sheet and the underside sheet, and a second layer comprises the same material as the upper side sheet of the first layer. The second layer thus may include a sheet of plastic bonded to the plastic upper side of the second layer. It is preferably attached by a continuously-running web process including stations that provide an interruptible heat-sealing process. This interruptible heat sealing process can be controlled to form elongated heat seals (e.g., 408D in FIG. 4D) that define the inflatable channels therebetween. The seals can be formed as continuous air impervious seals or discontinuous air permeable seals. The interruptible heat sealing process can be used to form the continuous seams, one of which is the seam at the peripheral of the first layer and the second layer. In some cases, the interruptible heat sealing process can be used to form the discontinuous heat seals. In some cases, absorbent material can be applied to the convective device, for example, applied as a single material layer. The absorbent material can be bonded to the upper plastic layer by heat processing or by adhesive bonding.

In some embodiments, the convective device is enabled to bathe a patient in the thermally controlled inflating medium introduced into the convective device 100, when inflated, via an air permeable layer. A layer can be air permeable using various materials or mechanical structures, for example, air-permeable materials, apertures, interstices, slits, or the like. In some implementations of an air permeable sheet with apertures, the density of apertures can vary among areas and/or inflatable sections.

In some embodiments, one or two layers of a convective device are made from a polyolefin non-woven extrusion coated, each with a coating of polypropylene on one side. In some other embodiments, the one or more layers can be poly lactic acid spunbond with polyolefin based extrusion coat. One of the layers may have holes formed by punching, slitting, or cutting to permit the flow of pressurized inflating medium from the inflated section through the layer. In some cases, the holes can be opened through both layers. In some cases, when the convective device is assembled, the polypropylene-coated side of the first layer is sealed to the polypropylene-coated side of the second layer at the periphery, and at the one or more locations to form the construction. The sealing process can use various techniques, for example, ultrasonic welding, radio frequency welding, heat sealing, or the like. Alternatively, the first layer and second layer may each include a laminate of polypropylene and polyolefin web with holes formed in at least one of the layers to support passage of pressurized air. In yet another embodiment, at least one of the layers can use air permeable material, for example, spunbond-meltblown-spunbond (SMS) nonwoven material; or the like.

Figure 5A:
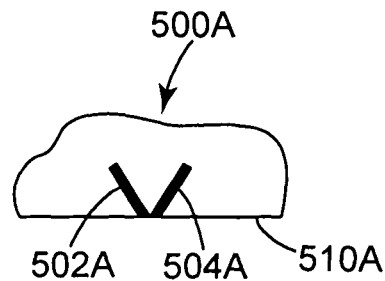
FIGS. 5A-5H illustrate some examples of air-guide devices.
Figure 5B:
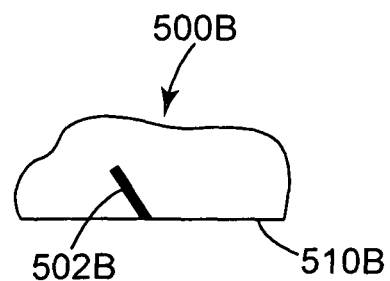
Figure 5C:
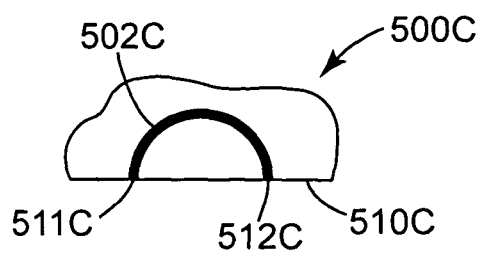
Figure 5D:
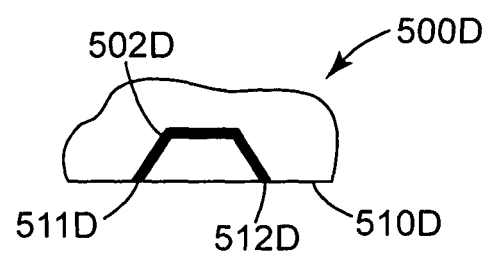

FIGS. 5A-5H illustrate some examples of air-guide devices/air-guide elements. FIG. 5A illustrates an air-guide device or air-guide element 500A including two guiding seals 502A and 504A, where both seals are extending from a periphery seal 510A. FIG. 5B illustrates an air-guide device or air-guide element 500B including one guiding seal 502B extending from a periphery seal 510B. FIG. 5C illustrates an air-guide device or air-guide element 500C including a continuous seal 502C, in a curve shape, starting from a first position 511C on a periphery seal 510C and ending at a second position 512C on the periphery seal 510C different from the first position 511C. When the convective device is inflated, the air-guide device 500C can facilitate forming a number of creases proximate to the air-guide device 500C in the convective device where the convective device is bent. FIG. 5D illustrates an air-guide device or air-guide element 500D including a continuous seal 502D starting from a first position 511D on a periphery seal 510D and ending at a second position 512D on the periphery seal 510D different from the first position 511D.

Figure 5E:
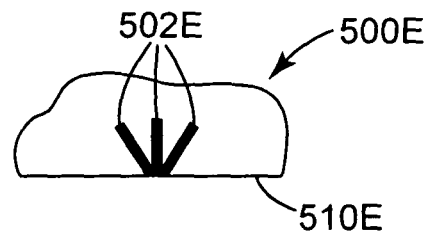
Figure 5F:
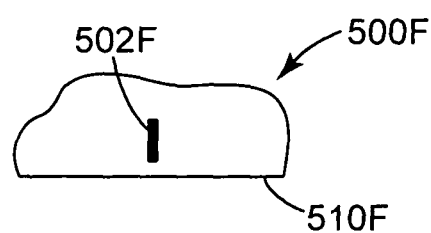
Figure 5G:
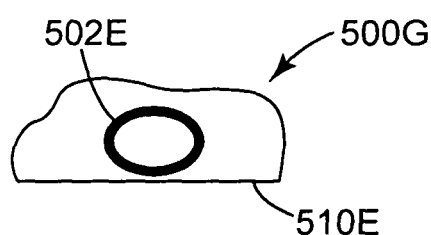

FIG. 5E illustrates an air-guide device or air-guide element 500E including three guiding seals 502E extending from a periphery seal 510E. FIG. 5F illustrates an air-guide device or air-guide element 500F including one seal 502F disposed proximate to but not touching a periphery seal 510F. FIG. 5G illustrates an air-guide device or air-guide element 500G including one continuous seal 502G in a closed shape or a closed shape seal 502G disposed proximate to but not touching a periphery seal 510G. The seal 502G can be in any closed shapes, for example, such as circle, oval, square, rectangle, polygon, or the like. In some cases, the seal 502G is no more than one inch (2.54 cm) from the periphery seal 510G. In some cases, the seal 502G is no more than two inches (5.08 cm) from the periphery seal 510G.

Figure 5H:
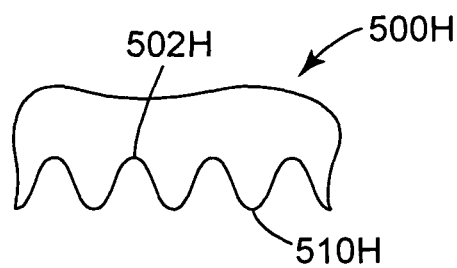

FIG. 5H illustrates an example of air-guide device 500H that is an integrated part of or proximate to a periphery seal 510H. The air-guide device 500H includes a zigzag portion 502H between first and second portions of the pneumatic structure as illustrated in FIGS. 1A, 2A and 3A, for example, such that the zigzag portion 502H is adapted to facilitate the generation of a number of distributed creases and direct inflation medium to reduce pressure drop of the inflation medium at the bending area when the configurable convective device is inflated and at least one of the first portion and the second portion are rearranged such that the inflatable channel between the two portions is bent. In some cases, the zigzag portion 502H is integrated with the periphery seal 510H. In some cases, the entire periphery seal can be zigzagged. In some cases, the zigzag portion 502H is in a wavy shape. In some cases, the zigzag portion is a in a curve shape, square saw-tooth, triangular saw-tooth, or similar shape, or combination of shapes.

Figure 6A:
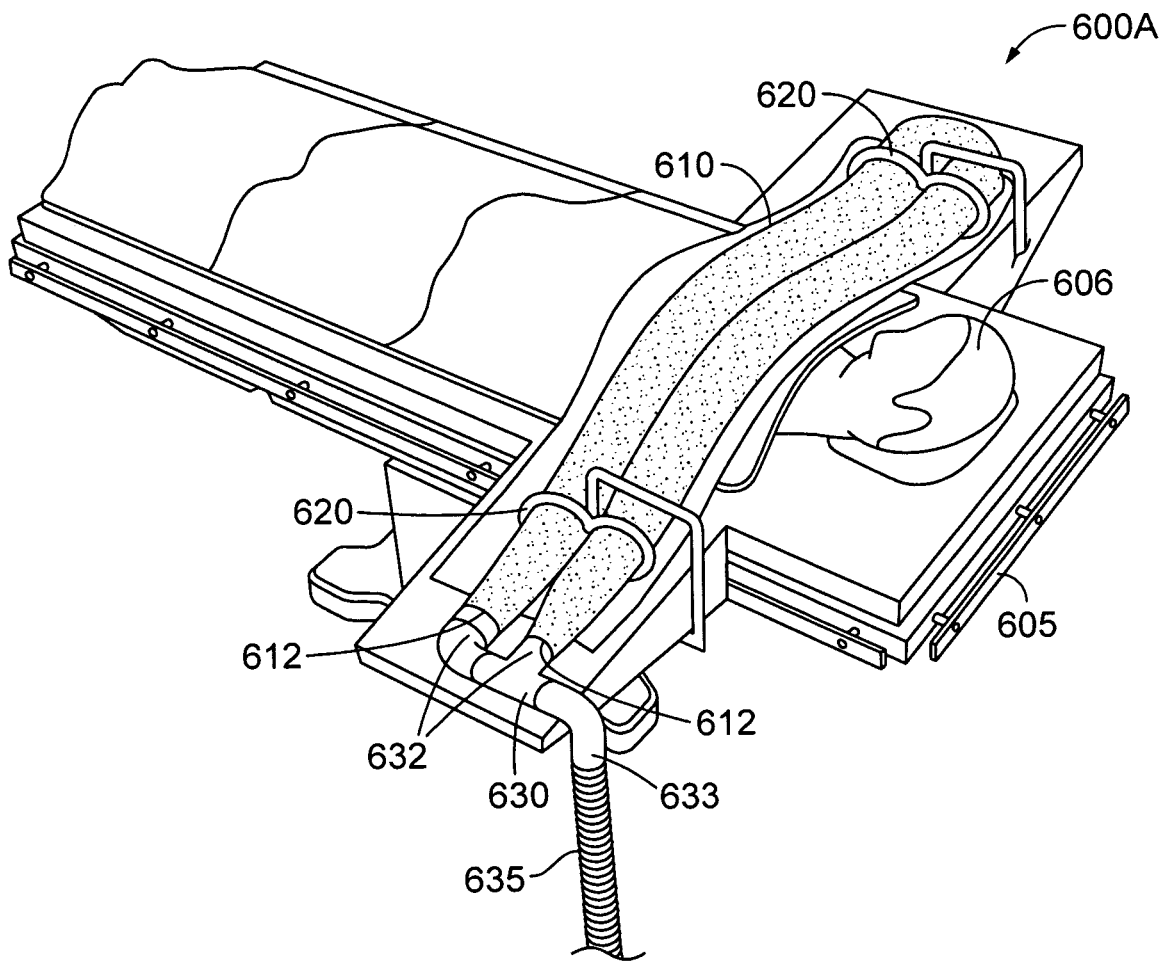
FIGS. 6A and 6B illustrate some examples of tubular convective systems.

In some embodiments, a convective system may include one or more fixation elements and/or hose manifold, as illustrated in FIG. 6A. In the example illustrated, a convective system 600A includes an inflatable tubular convective device 610, two fixation elements 620, and a hose manifold 630 configured to connect to a hose 635. The convective system 600 can be used with a bed 605. The tubular convective device 610 can be used on a person 606, for example, over the upper body of the person 606, over the lower body of the person 606, over the entire body of the person, or alongside the person 606. The fixation element 620 can be used to manage the disposition and shape of the convective device 610. For example, the convective device can be formed into a generally rectangular shape. As another example, the convective device can be formed into a "U" shape to be disposed alongside the person 606. In some cases, the fixation element 620 includes a first ring, where the first ring is configured to secure a first part of the tubular convective device 610. In the embodiment illustrated in FIG. 6A, the fixation element 620 further includes a second ring connected to the first ring, and wherein the second ring is configured to secure a second part of the tubular convective device.

In some cases, the convective device 610 can have two openings 612. In some cases, the hose manifold 630 is rigid. The hose manifold 630 includes a hose connector 633 configured to connect to a hose and two outlet connectors 632 configured to connect to the two openings 612 of the convective device 610 respectively, where the hose connector 633 and the two output connectors 632 are in fluid connection.

Figure 6B:
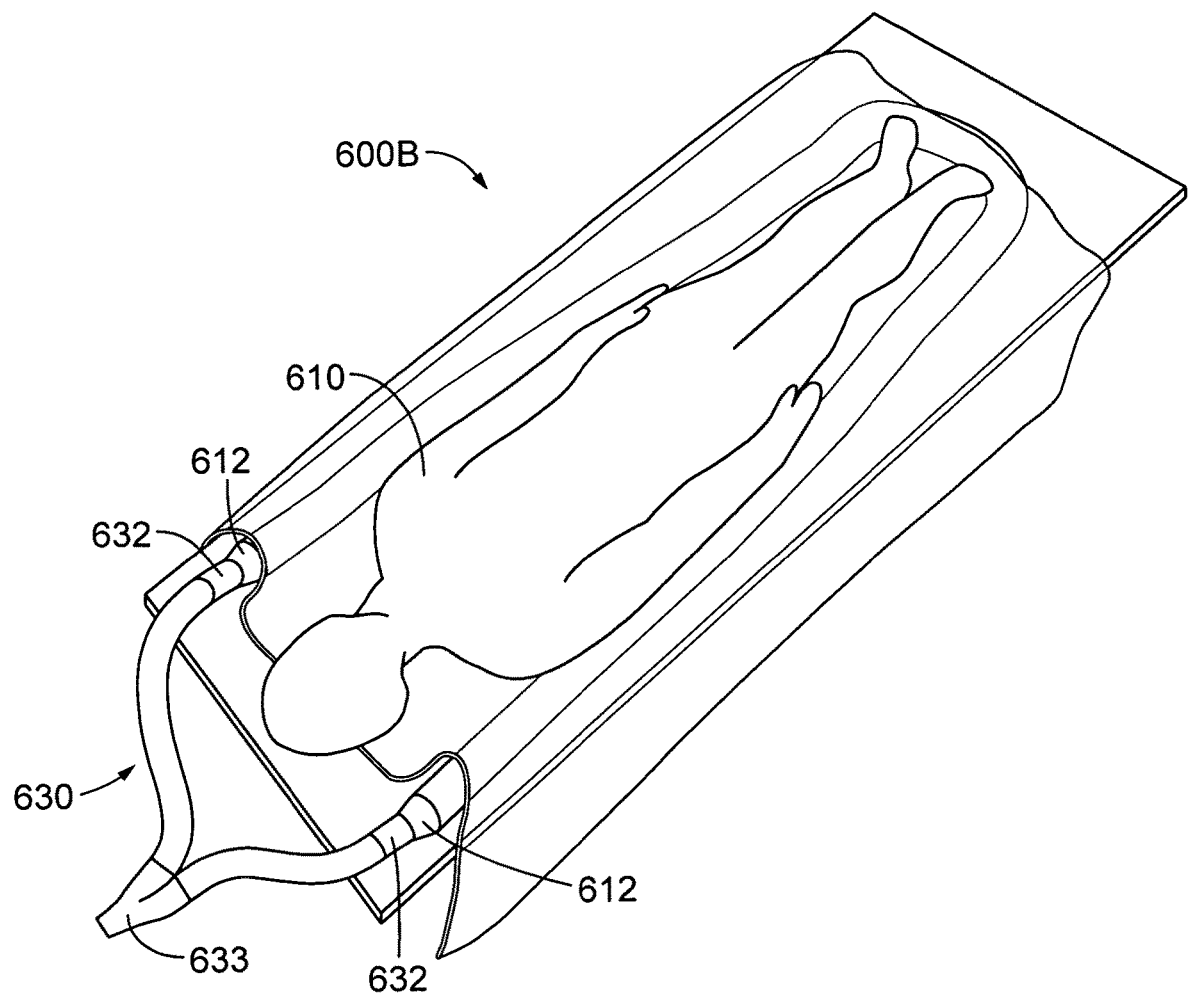

FIG. 6B illustrates another example of a convective system 600B. In the example illustrated, a convective system 600B includes an inflatable tubular convective device 610, and a hose manifold 630 configured to connect to a hose (not illustrated). In this embodiment, the hose manifold 630 includes two expandable outlet connectors 632 that can be connected to two openings 612 of the tubular convective device 610 and a hose connector 633 to connect to the hose.

Figure 7C:
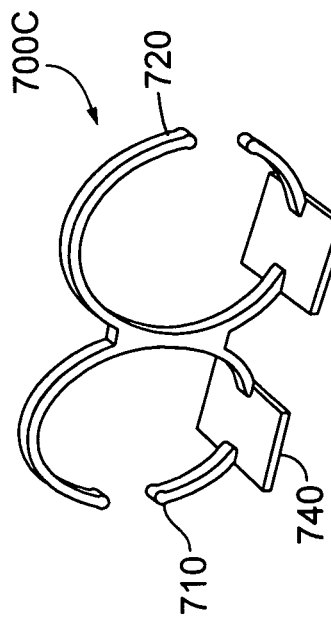
FIGS. 7A-7G illustrate some examples of fixation elements.
Figure 7D:
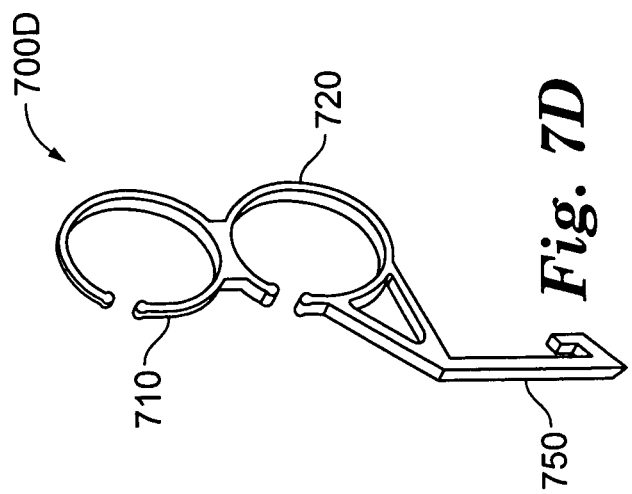
Figure 7A:
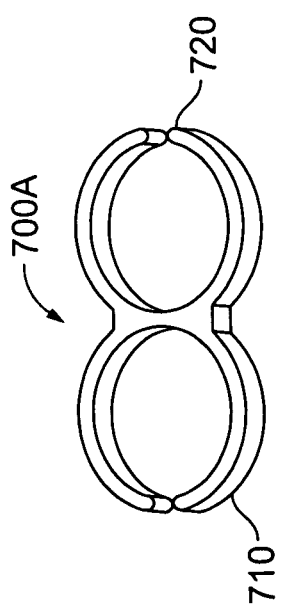
Figure 7B:
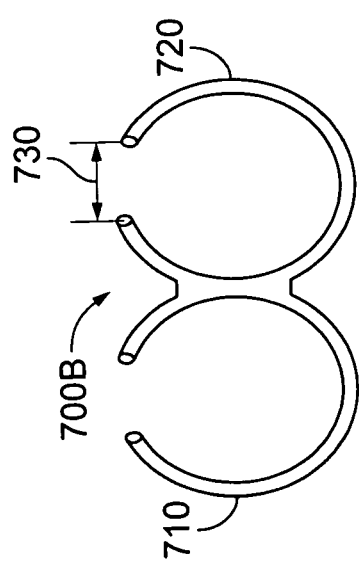

FIGS. 7A-7G illustrate some examples of fixation elements. FIG. 7A illustrates a fixation element 700A includes a first ring 710 and a second ring 720 connected to the first ring 710. FIG. 7B illustrates a fixation element 700B includes a first ring 710 and a second ring 720 connected to the first ring 710. In the example as illustrated, the first ring 710 and/or the second ring 720 has an opening 730. In some cases, the width of the opening 730 is less than the diameter of the corresponding ring.

FIG. 7C illustrates a fixation element 700C includes a first ring 710 and a second ring 720 connected to the first ring 710, and one or two generally flat elements 740, which can be used for placement. FIG. 7D illustrates a fixation element 700C includes a first ring 710 and a second ring 720 connected to the first ring 710, and an attachment element 750 configured to attach to a fixture, for example, such as an operation bed, an arm rest, a hospital bed, or the like. In the example illustrated, the attachment element 750 includes a generally "L" shape part.

Figure 7F:
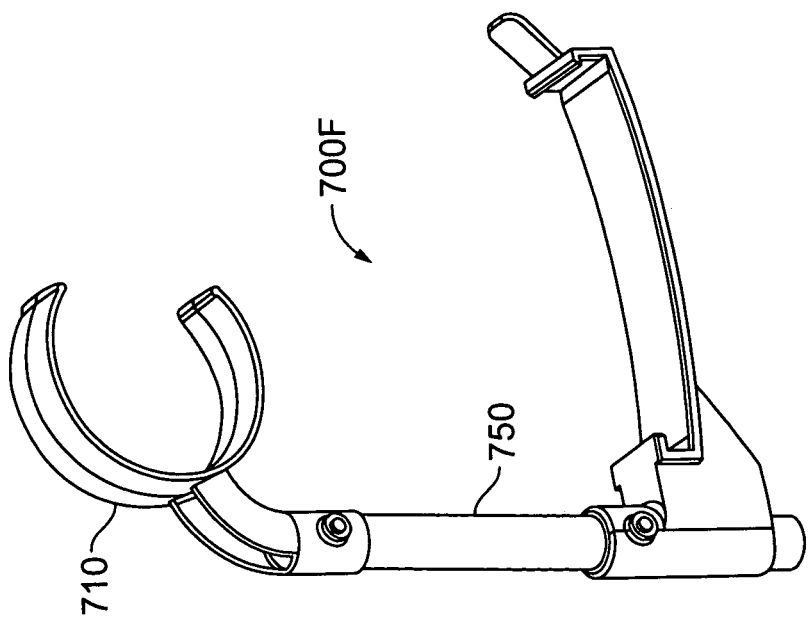
Figure 7E:
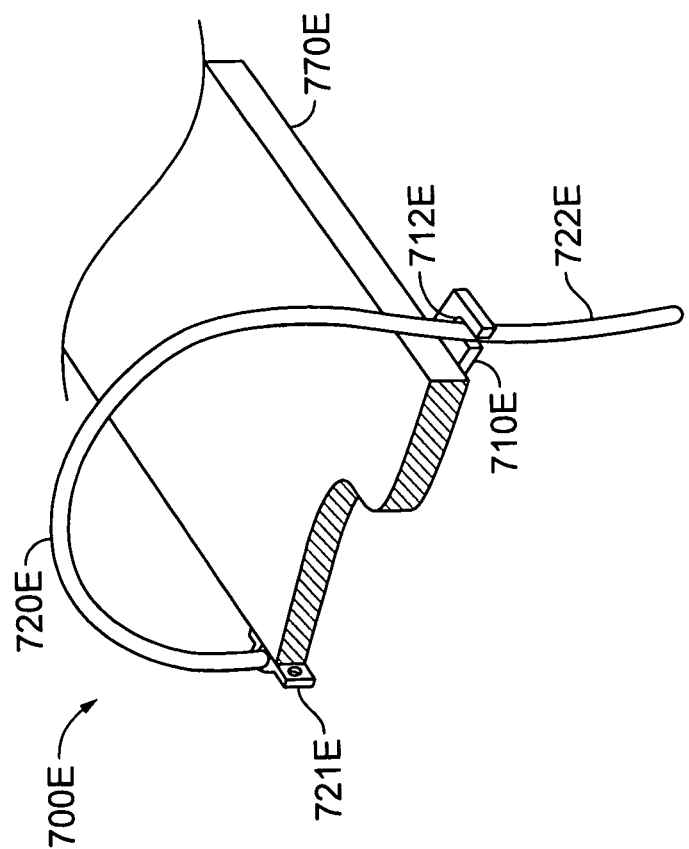

FIG. 7E illustrates a fixation element 700E including a rigid flat element 710E and a flexible element 720E configured to secure a part of a convective device. In some cases, the flexible element 720E is attached to the flat element 710E on one end 721E and the flat element 710E is configured to releasably attach to the flexible element 720E proximate to the other end 722E. For example, the flat element 710E has a slit 712E allowing the other end 722E of the flexible element 720E to slide in. In some other cases, the flexible element 720E can be attached to the flat element 710E on one end 721E and having a heavy part at the other end 722E such that the flexible element 720E can wrap around a convective device. In some cases, the flexible element 720E can be of any shapes, for example, a tube, a string, a flat string, a strap, or the like. In some implementations, the flat element 710E can be inserted into an arm rest 770E of an OR bed. In such implementations, the flat element 710E can have attachment elements (not shown) for placement, such as adhesive stripes, hook and loop, repositionable adhesives, mechanical reclosable fasteners, or the like.

Figure 7G:
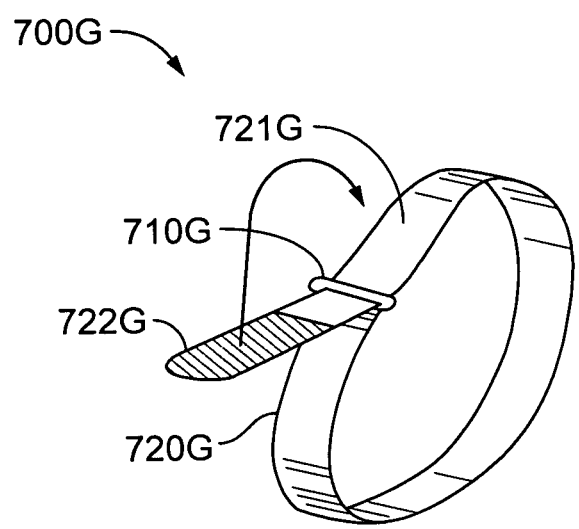

FIG. 7F illustrates an example of a fixation element 700F includes a first ring 710 and an attachment element 750 configured to attach to a fixture, for example, such as an operation bed, an arm rest, a hospital bed, or the like. In the example illustrated, the attachment element 750 includes a generally "L" shape part. FIG. 7G illustrates an example of a fixation element 700G having a ring 710G and a strap 720G. In some cases, the strap 720G can have an attachment element 721G on one end and a mating attachment element 722G on the other end. For example, the attachment elements (721G, 722G) can include, for example, hook and loop, adhesive strip, or the like.

FIGS. 8A and 8B illustrate two examples of hose manifolds used with tubular convective devices. FIG. 8A illustrates a hose manifold 800A including two outlet connectors 810A and 820A and a hose connector 830A configured to connect to a hose. As illustrated, the two outlet connectors 810A and 820A are generally parallel and open toward generally same directions. Each outlet connector (810A, 820A) is connected with one end of a tubular convective device 805. FIG. 8B illustrates a hose manifold 800B including two outlet connectors 810B and 820B and a hose connector 830B configured to connect to a hose. The two outlet connectors 810B and 820B open toward generally opposite directions. Each outlet connector (810B, 820B) is connected with one end of a tubular convective device 805. In some embodiments, the outlet connectors 810B and 820B of a manifold can be connected to two openings of a convective device.

Figure 8C:
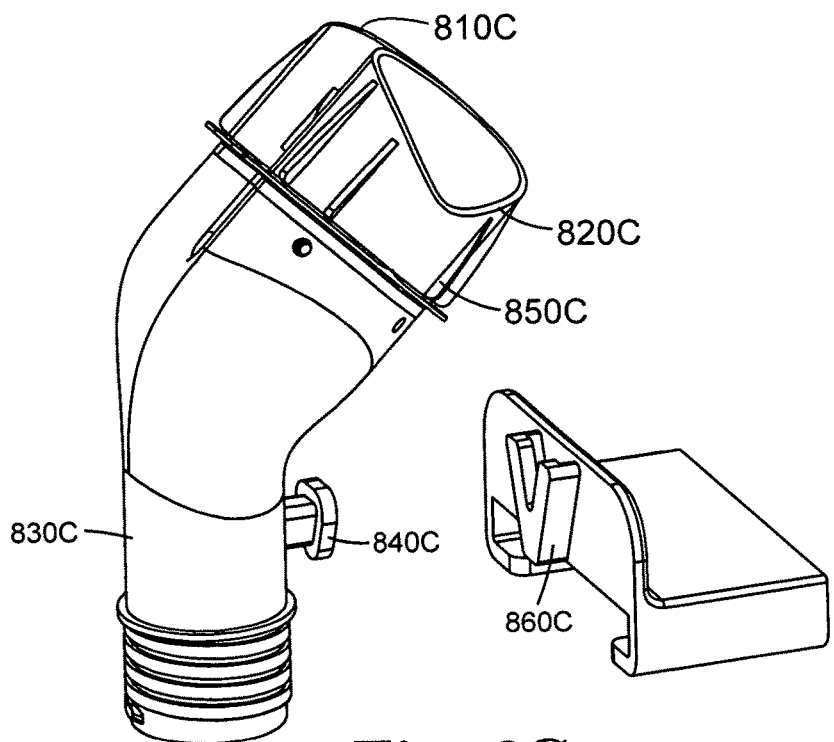
Figure 8D:
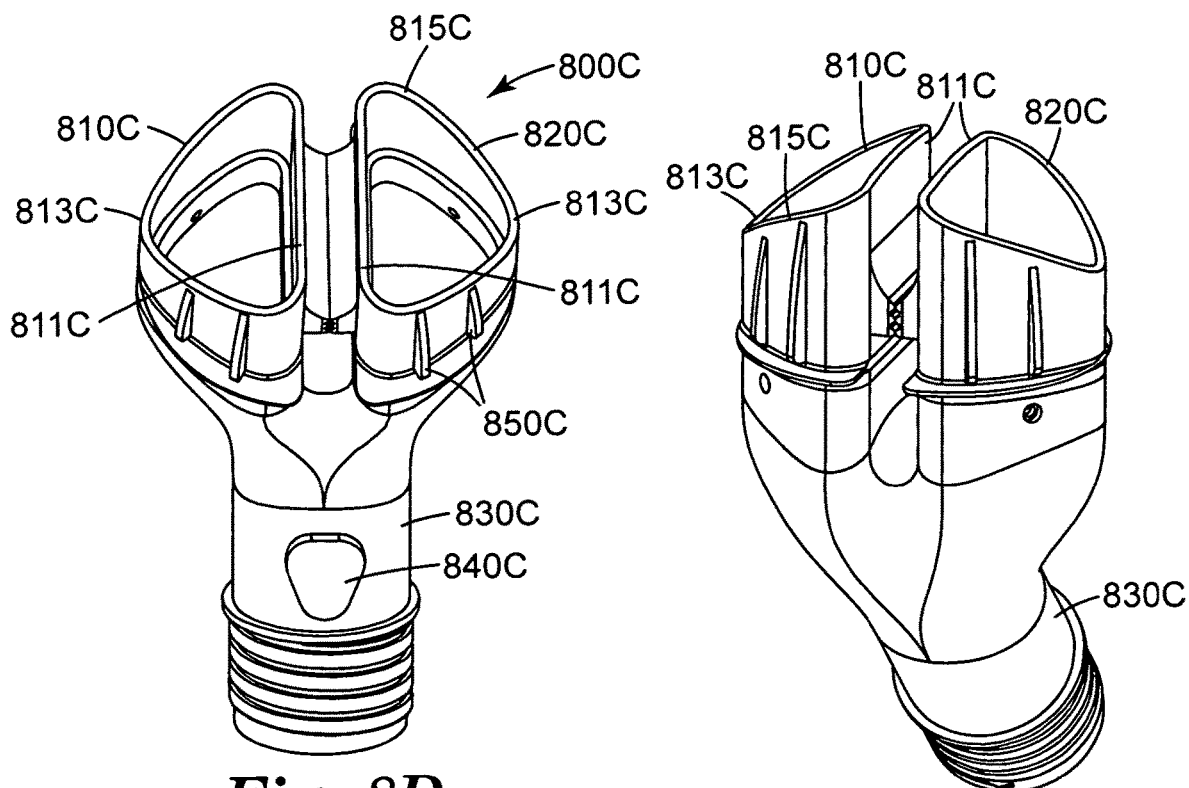
Figure 8E:
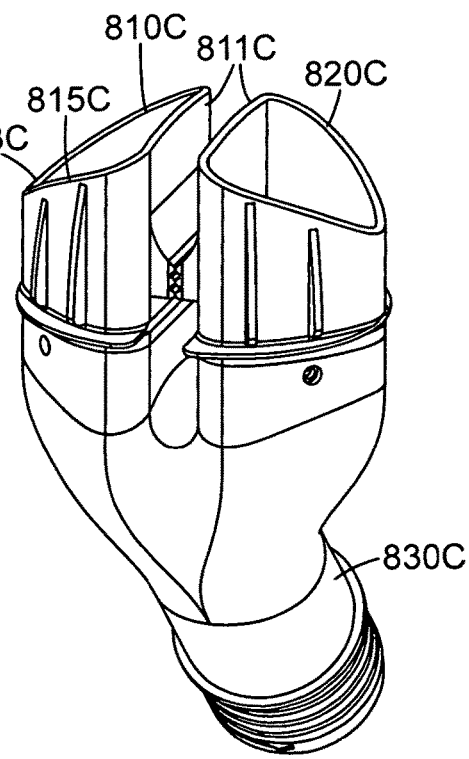

FIGS. 8C-8E illustrate another example of a hose manifold 800C, where FIG. 8C is a perspective view, FIG. 8D is a top view, and FIG. 8E is a side view. The manifold 800C includes two outlet connectors 810C and 820C and a hose connector 830C configured to connect to a hose. In some embodiments, the hose manifold 800C further includes an attachment element 840C configured to attach to a fixture. In some cases, the attachment element may include a generally "L" shape part. In the example illustrated, the attachment element 840C can include a "V" or triangle shape component, which can be inserted into a mating component (e.g., 860C) on the fixture. The cross-section of outlet connectors 810C and/or 820C can have any shapes, for example, a round shape, a triangular shape, an oval shape, a polygon shape, or the like. In some cases, the outlet connectors 810C and/or 820C can be slanted along a slope 815C. In some cases, the slope 815C is from the longest edge 811C toward the opposing tip 813C. In the example illustrated, the generally triangular shape opening and the slanted configuration may allow the connector to be easily inserted. In some embodiments, the connectors 810C and/or 820C can include one or more flexible flaps 850C that can prevent the connector from slipping out. In some cases, the flexible flap 850C can present leakage. An alternative structure to the flexible flap could also include a ridge or flange of flexible material with encircle the entire circumference of the hose manifold. Suitable materials of construction for the flexible flaps 850C, or the flexible ridge or flange structure would include soft or rigid thermoplastic elastomers such as polyesters, polyurethanes, polyamides, or polyolefin blends; or thermoset elastomers such as natural and synthetic rubbers such as latex, nitrile, millable polyurethane, silicone, butyl and neoprene.

Figure 8G:
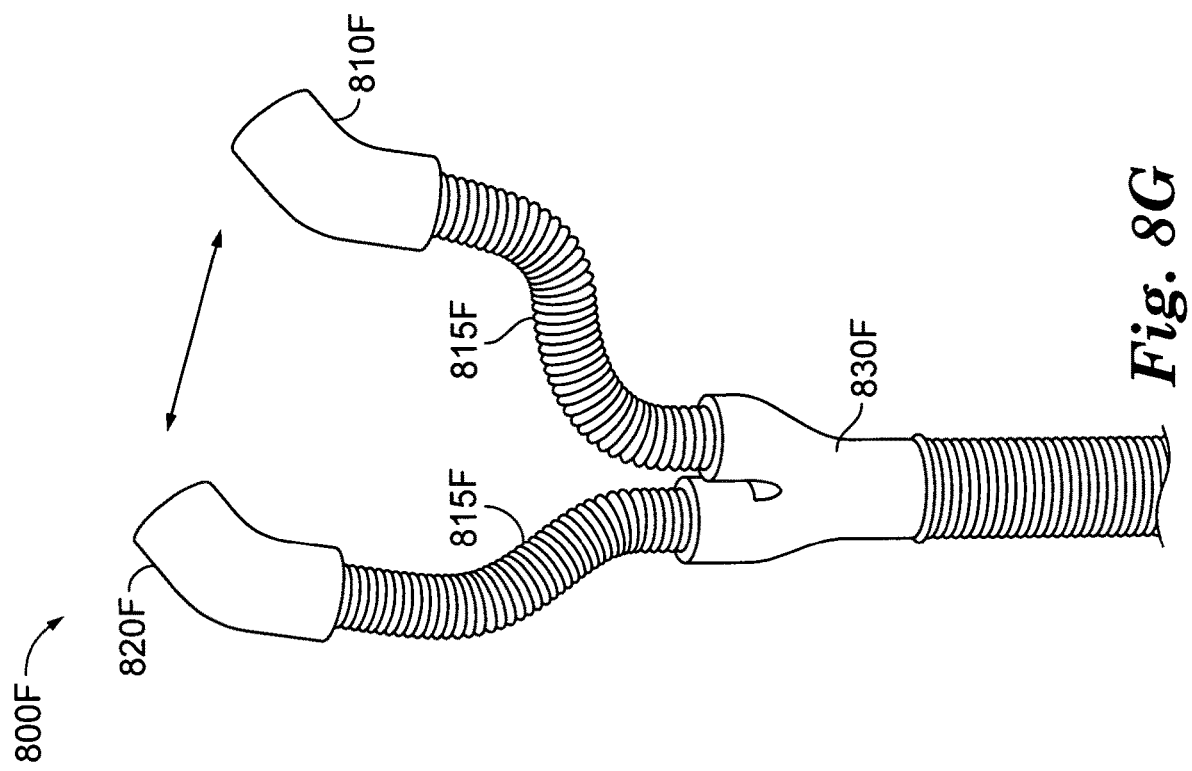
Figure 8F:
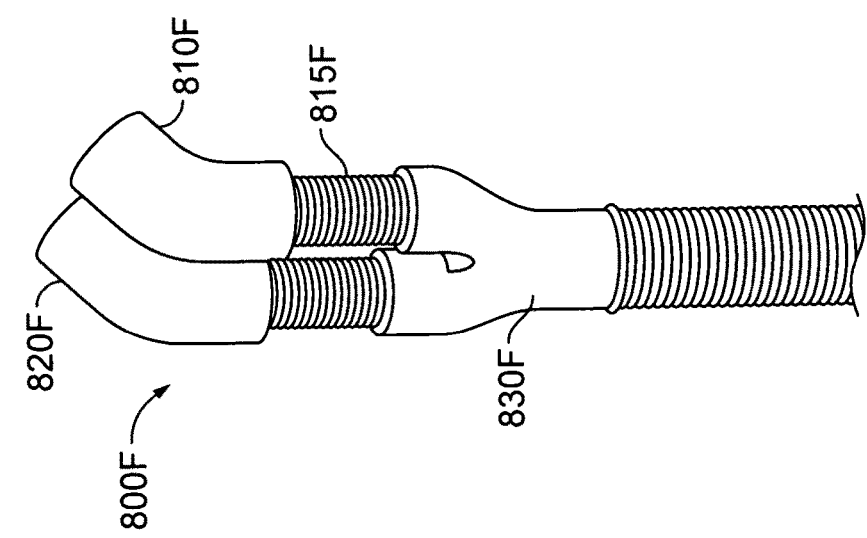

FIGS. 8F and 8G illustrate another example of a manifold 800F. The manifold 800F includes two outlet connectors 810F and 820F and a hose connector 830F configured to connect to a hose. One or both of the outlet connector (810F, 820F) can include an expandable element 815F. Expandable element 815F could be constructed of common thermoplastic or thermoset elastomers materials with an optional metal or rigid plastic coil to protect and reinforce expandable element from kinking or pinching that would close off the flow of inflating medium. FIG. 8G illustrates the expandable element 815F being extended such that the outlet connectors 810F and 820F are further apart. In some cases, the expandable element 815F can be expanded and retain the extension. In some embodiments, the expandable element 815F can be bent or rotated to an angle.

In some cases of using a convective device, a hose clamp may be used to maintain adequate air-tight connection between the hose and the convective device. FIG. 9A illustrates a perspective view of one embodiment of a hose clamp 900; and FIG. 9B illustrates a side view of the hose clamp 900. In the embodiment illustrated, the hose clamp 900 includes an encircling element 910, an optional grabbing component 920 extending from the encircling element, and an optional engaging component 930 disposed on or integrated with the encircling element. The encircling element 910 includes having an inner surface 912 and an opposing outer surface 914. In some cases, the central angle 950 of the encircling element 910 is greater than 180 degree. In some cases, the central angle 950 of the encircling element 910 is smaller than 360 degree.

In some embodiments, the engaging component 930 includes a plurality of engaging elements 935. In some implementations, the engaging component 930 includes a pattern of engaging elements 935, for example, a pattern of a line, a pattern of a wave, a pattern of higher density proximate to the end, or the like. The encircling element 910 has a first end 941, a second end 942, and a middle portion 945. In some cases, the encircling element 910 can be semi-rigid or rigid. The encircling element 910 can include materials, for example, polycarbonate, polyester, polyethylene, nylon, acrylonitrile butadiene styrene (ABS), polypropylene, polyvinyl chloride (PVC), and/or the like. In some cases, the grabbing component 920 and the engaging component 930 can include the same materials as the encircling element 910. In some other cases, the grabbing component 920 and the engaging component 930 can include different materials as the encircling element 910. In some cases, the engaging components can have a material the same as or different from the material used for the encircling element 910. In some cases, the engaging component 930 can use soft materials, for example, urethane, thermoplastic materials, thermoplastic elastomers (TPE), or the like. The engaging elements 935 can have any shapes, for example, cylinder, half sphere, prism, hexagonal prism, trapezoidal prism, cube, cuboid, cone, pyramid, or the like.

FIG. 9C illustrates a front view of another embodiment of a hose clamp 900C. The hose clamp 900C includes an encircling element 910, an optional grabbing component 920C extending from the encircling element, and an optional engaging component 930 disposed on or integrated with the encircling element. Components with same labels can have same or similar configurations, compositions, functionality and/or relationships as the corresponding components in FIGS. 9A and 9B. In the embodiment illustrated, the grabbing component 920C includes two elements 921 and 922.

Figure 10A:
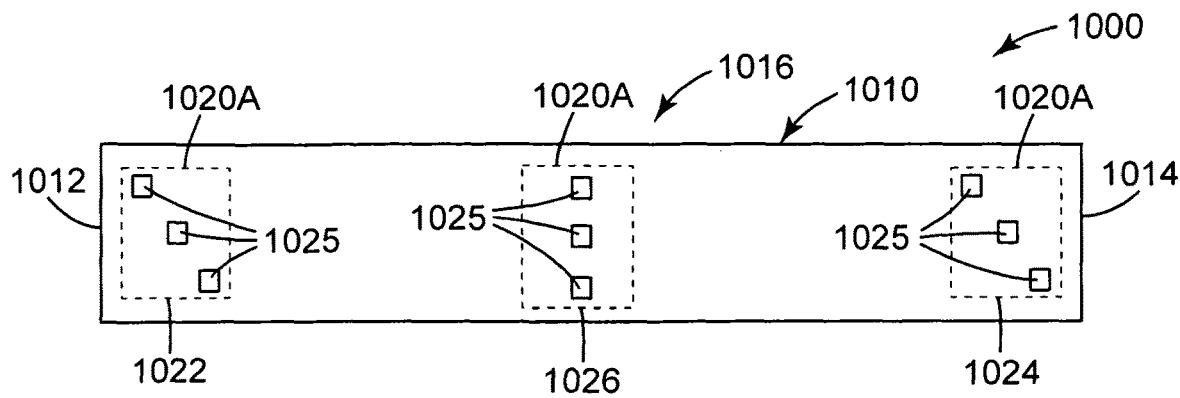
FIG. 10A is a flattened view of a hose clamp toward the inner surface of an encircling element.
Figure 10B:
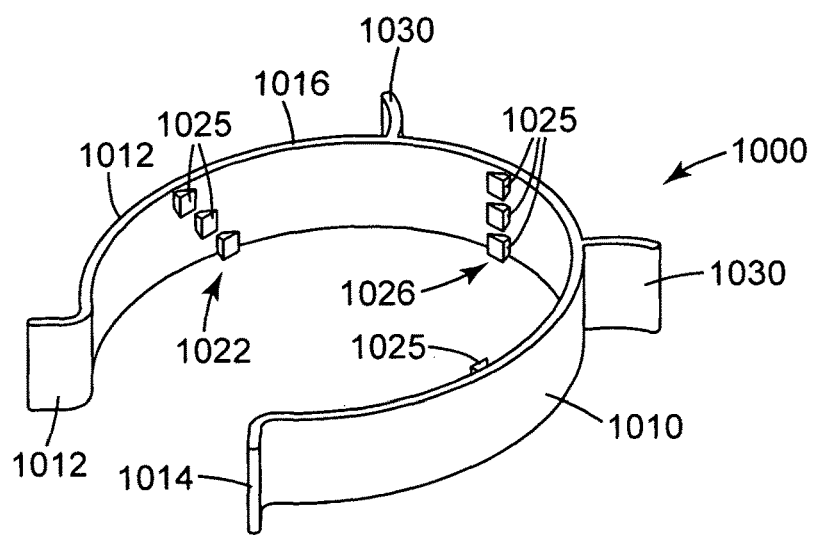
FIG. 10B is a perspective view of the hose clamp illustrated in FIG. 10A.
Figure 10C:
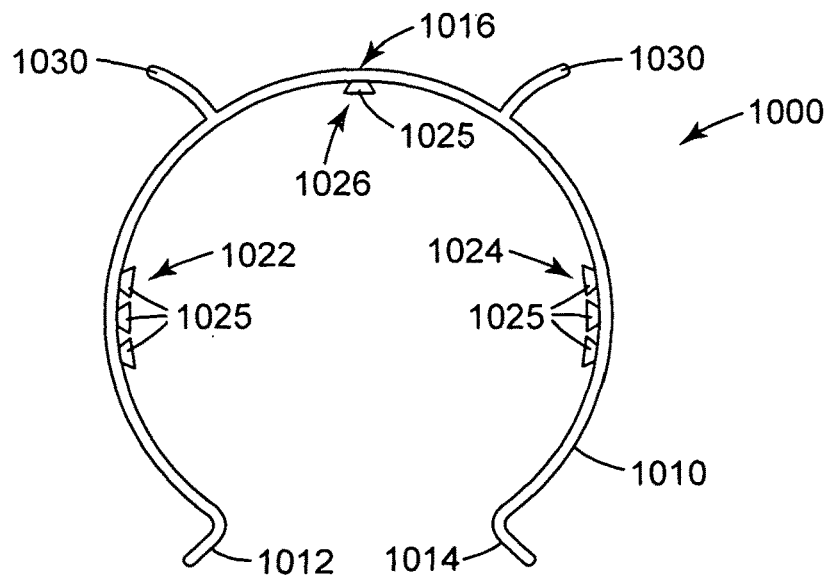
FIG. 10C is a side view of the hose clamp illustrated in FIG. 10A.

FIG. 10A is a flattened view of a hose clamp 1000 toward the inner surface of an encircling element; FIG. 10B is a perspective view of the hose clamp 1000; and FIG. 10C is a side view of the hose clamp 1000. The hose clamp 1000 includes an encircling element 1010, an optional grabbing component 1030 and an optional engaging component 1020A. The encircling element 1010 has a first end 1012, a second end 1014, and a middle portion 1016. The engaging component 1020A can include one or more sets of engaging elements 1025. In one embodiment, the engaging component 1020A includes a set of engaging elements 1022 disposed proximate to the first end 1012 of the encircling element 1010. In the example illustrated in 10A, the set of engaging elements 1022 includes multiple engaging elements 1025 (with three illustrated) disposed in a line, where the engaging elements 1025 are disposed in a line slanted from the first end 1012. In some embodiments, the engaging component 1020A includes a set of engaging elements 1024 disposed proximate to the second end 1014 of the encircling element 1010. In the example illustrated in FIG. 10A, the set of engaging elements 1024 includes multiple engaging elements 1025 disposed in a line, where the engaging elements 1025 are disposed in a line slanted from the second end 1014. In some embodiments, the engaging component 1020A includes a set of engaging elements 1026 disposed in the middle portion 1016. In some cases, the set of engaging elements 1026 includes at least three engaging elements 1025 disposed in a line.

Figure 10D:
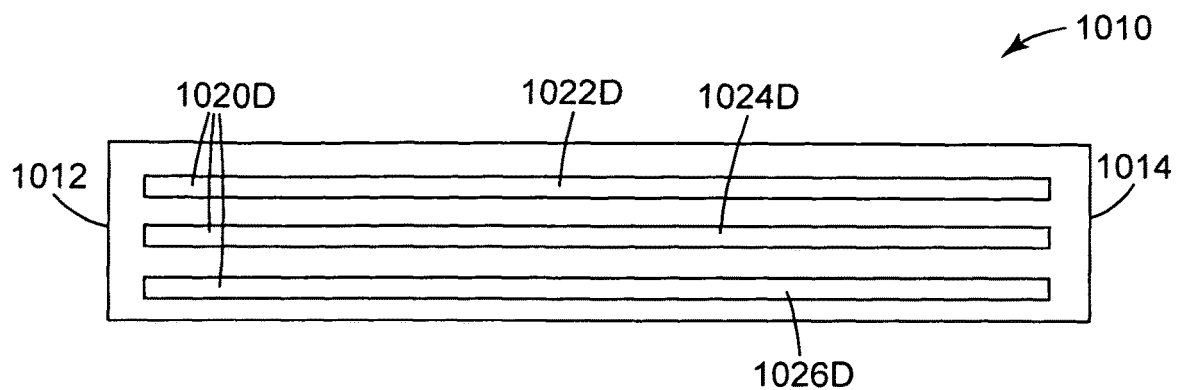
FIGS. 10D-10G illustrate some example configurations of engaging components.
Figure 10E:
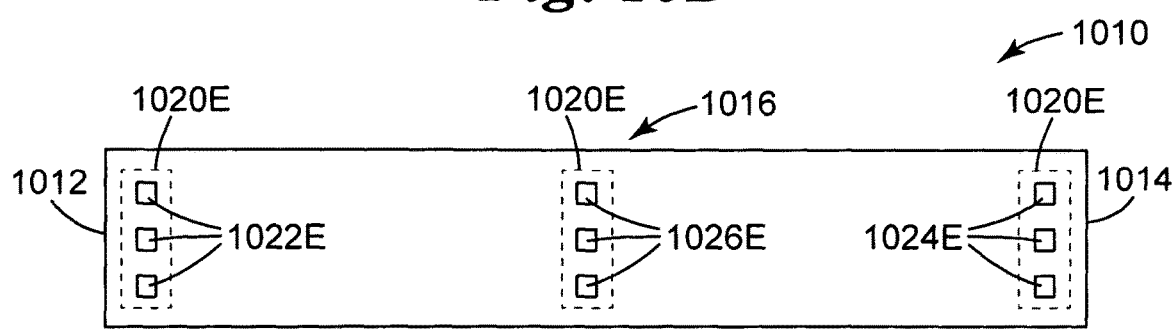

FIGS. 10D-10G illustrate some example configurations of engaging components. FIG. 10D illustrates an engaging component 1020D includes three elongated engaging elements 1022D, 1024D, and 1026D that are generally parallel with each other and extend proximate the first end 1012 to the second end 1014. FIG. 10E illustrates an engaging component 1020E includes three sets of engaging elements (1022E, 1024E, and 1026E). The set of engaging element 1022E is proximate to the first end 1012 and is in a line. The set of engaging element 1024E is proximate to the second end 1014 and is generally in a line. The set of engaging element 1026E is proximate to the center portion 1016 and is generally parallel to either end.

Figure 10F:
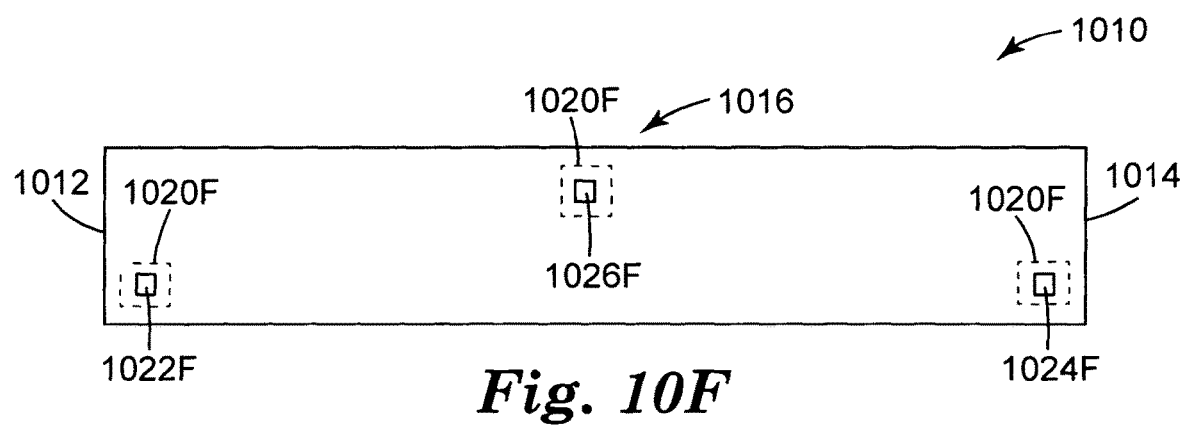
Figure 10G:
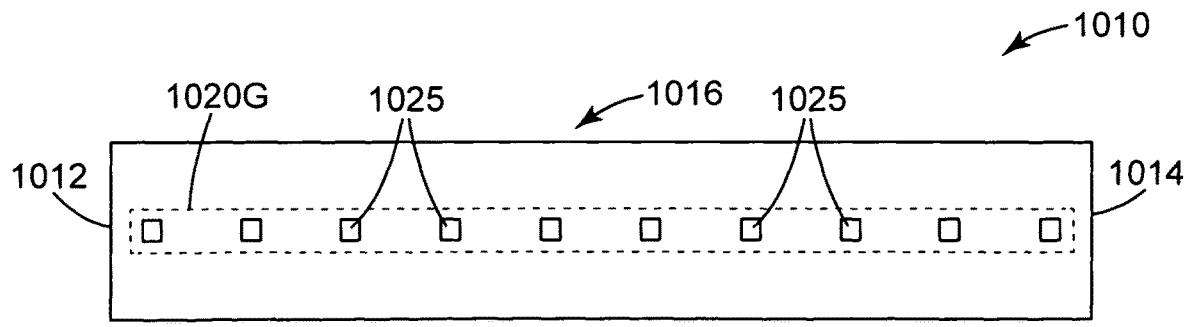

FIG. 10F illustrates an engaging component 1020F including three engaging elements (1022F, 1024F, and 1026F). The engaging element 1022F is disposed proximate to the first end 1012, the engaging element 1024F is disposed proximate to the second end 1014, and the engaging element 1026F is disposed at the center portion 1016. The three engaging elements 1022F, 1024F, and 1026F, as illustrated, may be disposed at locations with different distances to the edges of the encircling element 1010. FIG. 10G illustrates an engaging component 1020G including multiple engaging elements 1025. In one embodiment, the engaging elements 1025 can be disposed discontinuously across the encircling element 1010 from the first end 1012 to the second end 1014.

Figure 11:
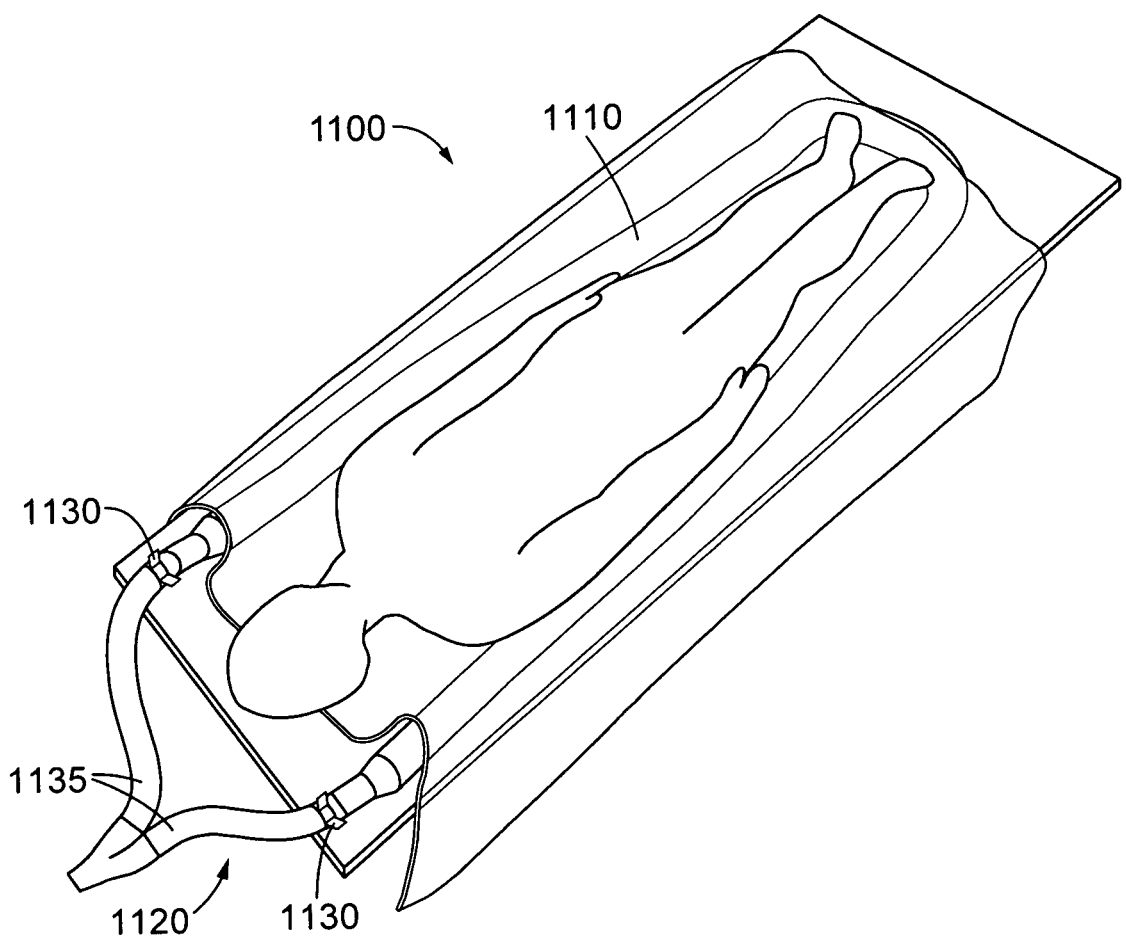
FIG. 11 illustrates an example of a convective system.

FIG. 11 illustrates an example of a convective system 1100. The convective system 1100 includes a tubular convective device 1110, a hose manifold 1120, and one or more hose clamps 1130. The tubular convective device, the hose manifold, and the hose clamp can use any one of the configurations of respective devices and components described in the present disclosure. The tubular connective device 1110 is connected to the hose manifold 1120 and the hose clamp 1130 is applied on top of the connection portion of the tubular connective device 1110 and the hose manifold 1120 to maintain the generally airtight connection. In the example illustrated, the hose manifold 1120 includes two outlet connectors 1135.

Figure 12A:
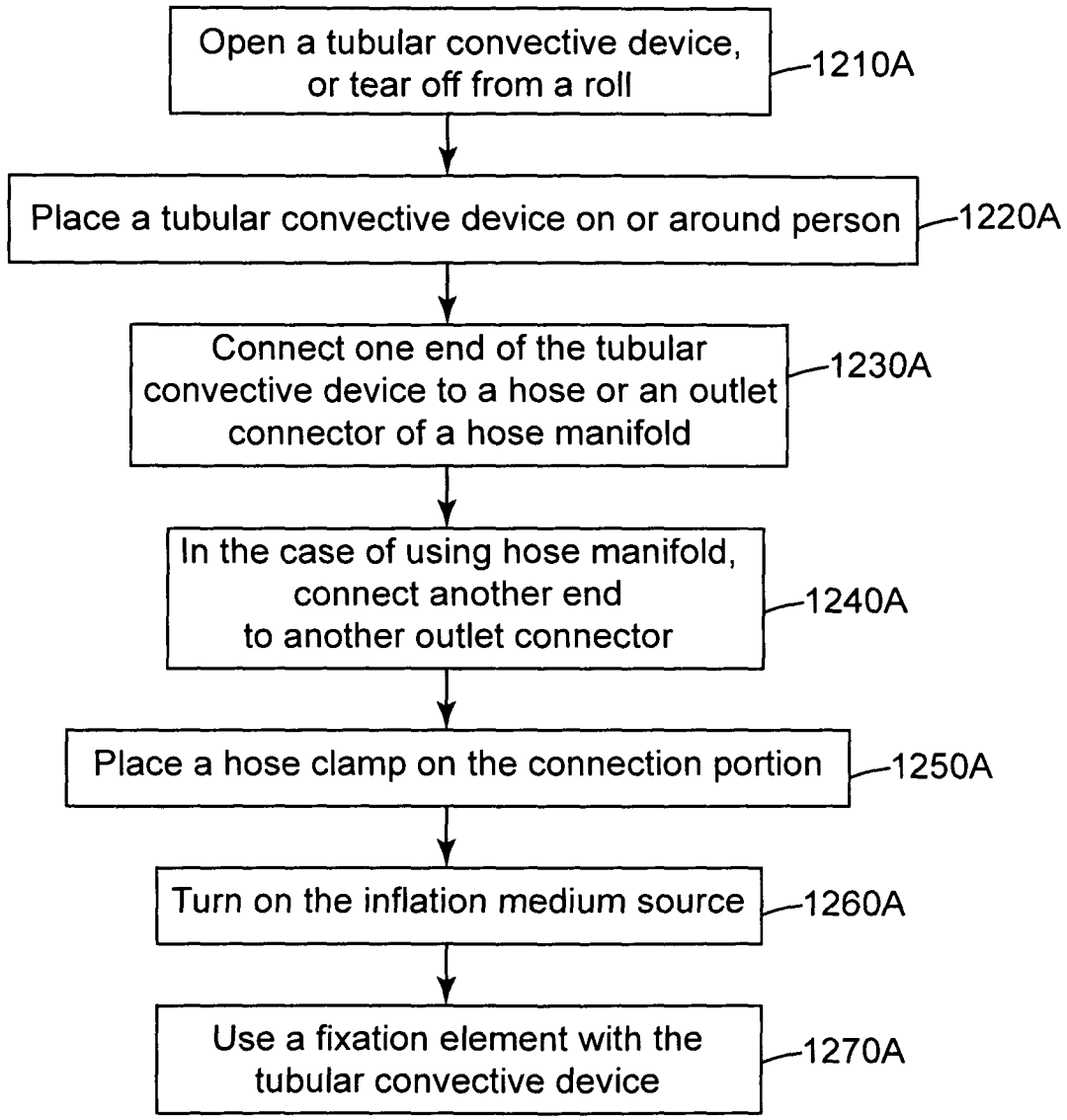
FIG. 12A illustrates an example flowchart of using a tubular convective device.

FIG. 12A illustrates an example flowchart of using a tubular convective device. First, open a tubular convective device, or tear off from a roll (step 1210A). Place a tubular convective device on or around a person (step 1220A). Next, connect one end of the tubular convective device to a hose or an outlet connector hose manifold (step 1230A). Optionally, in the case of using a hose manifold, connect another end of the tubular convective device to another outlet connector of the hose manifold (step 1240A). Optionally, place a hose clamp on the connection portion between the hose or hose manifold and the tubular convective device (step 1250A). Turn on the inflating medium source (step 1260A). Optionally, use a fixation element with the tubular convective device (step 1270A), for example, to keep the tubular convective device close to the person or cover a specific part of the person.

Figure 12B:
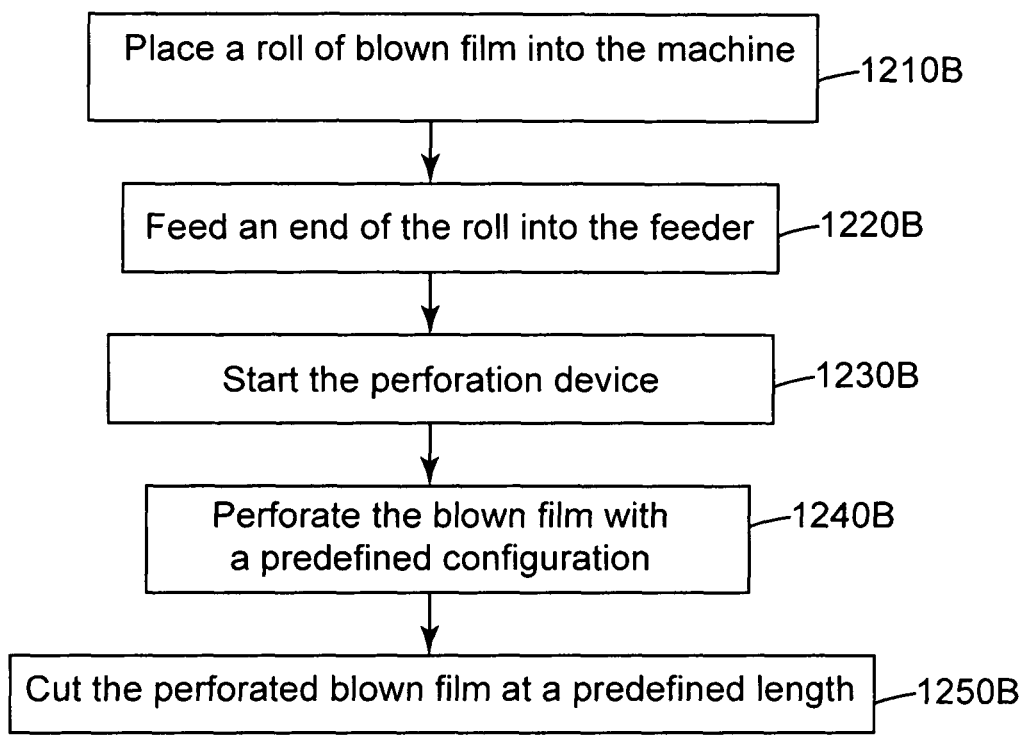
FIG. 12B illustrates an example flowchart of making a tubular convective device.

FIG. 12B illustrates an example flowchart of making a tubular convective device. Place a roll of blown film into the machine (step 1210B). Place an end of the roll into the feeder (step 1220B). Optionally, start the perforation device (step 1230B). Perforate the blown film with a predefined configuration (step 1240B). Optionally, cut the perforated blown film at a predefined length (step 1250B). In some cases, a measurement device can be used. The measurement device can be, for example, a ruler, one or more markers indicating various length, or the like. In some cases as illustrated in FIG. 1B, the blown film is laid flat to feed into the machine, such that the perforation is done on the two layers of film. In some cases, the perforation device has a density of at least 1500 pins per square meter.

Exemplary Embodiments

Item A1. A tubular convective system, comprising:
an inflatable tubular convective device, comprising:
a tubular structure comprising a flexible material, wherein at least part of the tubular structure is air permeable;
a fixation element comprising a first ring, wherein the first ring is configured to secure a first part of the tubular convective device.

Item A2. The tubular convective system of Item A1, wherein the fixation element further comprises a second ring connected to the first ring, and wherein the second ring is configured to secure a second part of the tubular convective device.

Item A3. The tubular convective system of Item A1 or A2, wherein the first ring has an opening.

Item A4. The tubular convective system of Item A3, wherein a width of the opening is less than a diameter of the first ring.

Item A5. The tubular convective system of any one of Item A1-A4, wherein the fixation element further comprises a generally flat element.

Item A6. The tubular convective system of any one of Item A1-A5, wherein the fixation element further comprises an attachment element configured to attach to a fixture.

Item A7. The tubular convective system of Item A6, wherein the attachment element comprises a generally "L" shape part.

Item A8. The tubular convective system of any one of Item A1-A7, wherein the tubular convective device further comprises an air-guide element configured to direct flow of inflating medium when the tubular convective device is bent.

Item A9. The tubular convective system of Item A8, wherein the air-guide element comprises a guiding seal extending from an edge of the tubular convective device toward the tube structure.

Item A10. The tubular convective system of Item A8, wherein the air-guide element is disposed within the tube structure.

Item A11. The tubular convective system of Item A8, wherein the air-guide element is configured to facilitate forming creases at the edge of the air-guide element when the tubular convective device is inflated and bent.

Item A12. The tubular convective system of any one of Item A1-A11, wherein the tubular structure comprises a blown film.

Item A13. The tubular convective system of Item A12, wherein the tubular structure further comprises a plurality of apertures disposed on the blown film.

Item A14. The tubular convective system of Item A13, wherein the tubular structure comprises a first portion and a second portion separated from the first portion longitudinally, and wherein the plurality of apertures are only disposed on the first portion of the tubular structure.

Item A15. A tubular convective system, comprising:
an inflatable tubular convective device, comprising:
a tubular structure comprising a flexible material, wherein at least part of the tubular structure is air permeable;
a fixation element comprising a flat element and a flexible element attached to the flat element proximate to a first end of the flexible element, wherein the flexible element is configured to secure a first part of the tubular convective device.

Item A16. The tubular convective system of Item A15, wherein the flat element is configured to releasably attach to the flexible element proximate to a second end of the flexible element.

Item A17. The tubular convective system of Item A16, wherein the flat element comprises a slit allowing the flexible element to slide in.

Item A18. The tubular convective system of any one of Item A15-A17, wherein the flexible element comprises a heavy component proximate to a second end.

Item A19. The tubular convective system of any one of Item A15-A18, wherein the flat element is configured to be secure to a fixture.

Item A20. The tubular convective system of any one of Item A15-A19, wherein the flexible element comprises at least one of a tube, a string, and a strap.

Item A21. The tubular convective system of any one of Item A15-A20, wherein the tubular convective device further comprises an air-guide element configured to direct flow of inflating medium when the tubular convective device is bent.

Item A22. The tubular convective system of Item A21, wherein the air-guide element comprises a guiding seal extending from an edge of the tubular convective device toward the tube structure.

Item A23. The tubular convective system of Item A21, wherein the air-guide element is disposed within the tube structure.

Item A24. The tubular convective system of Item A21, wherein the air-guide element is configured to facilitate forming creases at the edge of the air-guide element when the tubular convective device is inflated and bent.

Item A25. The tubular convective system of any one of Item A15-A24, wherein the tubular structure comprises a blown film.

Item A26. The tubular convective system of Item A25, wherein the tubular structure further comprises a plurality of apertures disposed on the blown film.

Item A27. The tubular convective system of Item A26, wherein the tubular structure comprises a first portion and a second portion separated from the first portion longitudinally, and wherein the plurality of apertures are only disposed on the first portion of the tubular structure.

Item B1. A convective system, comprising:
an inflatable convective device having a pneumatic structure and two openings into the pneumatic structure, wherein at least part of the convective device is air permeable;
a hose manifold comprising:
a hose connector configured to connect to a hose,
two outlet connectors configured to connect to the two openings respectively,
wherein the hose connector and the two output connectors are in fluid connection.

Item B2. The convective system of Item B1, wherein the two outlet connectors open toward generally opposite directions.

Item B3. The convective system of Item B1 or B2, wherein the two outlet connectors are generally parallel and open toward generally same directions.

Item B4. The convective system of any one of Item B1-B3, wherein the hose manifold further comprises an attachment element configured to attach to a fixture.

Item B5. The convective system of Item B1, wherein at least one of the two outlet connectors further comprises a flexible flap configured to prevent slipping.

Item B6. The convective system of any one of Item B1-B5, wherein at least one of the two outlet connectors is slanted.

Item B7. The convective system of any one of Item B1-B6, wherein at least one of the two outlet connectors comprises a generally triangular opening.

Item B8. The convective system of any one of Item B1-B7, wherein at least one of the two outlet connectors comprises a generally round opening.

Item B9. The convective system of any one of Item B1-B8, wherein at least one of the two outlet connectors comprises an expandable element.

Item B10. The convective system of any one of Item B1-B9, wherein the hose manifold is rigid.

Item B11. The convective system of any one of Item B1-B10, wherein the inflatable convective device further comprises an air-guide element configured to direct flow of inflating medium when the inflatable convective device is bent.

Item B12. The convective system of Item B11, wherein the air-guide element comprises a guiding seal extending from an edge of the inflatable convective device toward the pneumatic structure.

Item B13. The convective system of Item B11, wherein the air-guide element is disposed within the pneumatic structure.

Item B14. The convective system of Item B11, wherein the air-guide element is configured to facilitate forming creases at the edge of the air-guide element when the inflatable convective device is inflated and bent.

Item B15. The convective system of any one of Item B1-B14, wherein the inflatable convective device is a tubular convective device.

Item B16. The convective system of Item B15, wherein the tubular convective device comprises a blown film.

Item B17. The convective system of Item B16, wherein the tubular convective device further comprises a plurality of apertures disposed on the blown film.

Item B18. The convective system of Item B17, wherein the tubular convective device comprises a first portion and a second portion separated from the first portion longitudinally, and wherein the plurality of apertures are only disposed on the first portion of the tubular structure.

Item C1. A tubular convective device, comprising:
a blown film forming a tube when inflated, the blown film having a first portion and a second portion, wherein the first portion and the second portion are separated longitudinally, and
a plurality of apertures disposed on the first portion of the blown film.

Item C2. The tubular convective device of Item C1, wherein the first portion and the second portion are each half portion.

Item C3. The tubular convective device of Item C1 or C2, wherein the plurality of apertures are only disposed on the first portion of the blown film.

Item C4. The tubular convective device of any one of Item C1-C3, wherein the plurality of apertures are disposed on the second portion of the blown film.

Item C5. The tubular convective device of any one of Item C1-C4, further comprises: an air-guide element configured to direct flow of inflating medium when the tubular convective device is bent.

Item C6. The tubular convective device of Item C5, wherein the air-guide element comprises a guiding seal extending from an edge of the tubular convective device toward the tube structure.

Item C7. The tubular convective device of Item C5, wherein the air-guide element is disposed within the tube structure.

Item C8. The tubular convective device of Item C5, wherein the air-guide element is configured to facilitate forming creases at the edge of the air-guide element when the tubular convective device is inflated and bent.

Item C9. The tubular convective device of any one of Item C1-C8, wherein the tubular convective device is in a roll.

Item C10. A tubular convective system comprising:
the tubular convective device of Item C1,
a dispenser containing the tubular convective device.

Item C11. The tubular convective system of Item C10, wherein a dispenser comprises a cutting device.

Item C12. A tubular convective system, comprising:

a plurality of tubular convective devices, each tubular convective device comprising:
a tubular structure comprising a flexible material, and
a plurality of apertures on the tubular structure,
wherein adjacent two of the plurality of tubular convective devices are connected.

Item C13. The tubular convective system of Item C12, further comprises: a line of weakness between two adjacent tubular convective devices of the plurality tubular convective devices.

Item C14. The tubular convective system of Item C12 or C13, further comprises: an close seal between two adjacent tubular convective devices of the plurality tubular convective devices.

Item C15. The tubular convective system of Item C13, further comprises: an close seal between two adjacent tubular convective devices of the plurality tubular convective devices, wherein the close seal is disposed proximate to the line of weakness.

Item C16. The tubular convective system of any one of Item C12-C15, wherein two of the plurality of tubular convective devices have different length from each other.

Item C17. The tubular convective system of any one of Item C12-C16, wherein the plurality of tubular convective devices are in a roll.

Item C18. The tubular convective system of any one of Item C12-C17, wherein the tubular structure comprises a blown film.

Item C19. The tubular convective system of any one of Item C12-C18, wherein the tubular structure comprises a layer of flexible materials sealed at a longitudinal edge.

Item C20. The tubular convective system of any one of Item C12-C19, wherein the tubular structure comprises a first flexible layer and a second flexible layer, wherein the first flexible layer and the second flexible layer are sealed at two longitudinal edges.

Item C21. The tubular convective system of Item C20, wherein the plurality of apertures are disposed only on the first flexible layer.

Item C22. The tubular convective system of any one of Item C12-C21, wherein the tubular structure comprises a first portion and a second portion separated from the first portion longitudinally, and wherein the plurality of apertures are disposed only on the first portion.

Item C23. The tubular convective system of any one of Item C12-C22, wherein each tubular convective device comprises an attachment device.

Item C24. The tubular convective system of Item C23, wherein the attachment device comprises an adhesive strip.

Item C25. The tubular convective system of Item C23, wherein the attachment device comprises a plurality of adhesive segments disposed in a pattern.

Item C26. The tubular convective system of Item C25, wherein the plurality of adhesive segments are disposed in a generally equal spacing longitudinally.

Item C27. The tubular convective system of Item C23, wherein the attachment device of a tubular convective device is connected to the attachment device of an adjacent tubular convective device.

Item C28. A tubular convective system, comprises:
a tubular convective device comprising:
a tubular structure comprising a flexible material, and
a plurality of apertures on the tubular structure; and
a fixation element configured to secure a first part of the tubular convective device.

Item C29. The tubular convective system of Item C28, wherein the fixation element comprises a ring.

Item C30. The tubular convective system of Item C28 or C29, wherein the fixation element comprises a flat element and a flexible element attached to the flat element.

Item C31. The tubular convective system of any one of Item C28-C30, further comprises:
a hose manifold comprising: a hose connector configured to connect to a hose, two outlet connectors configured to connect to two ends of the tubular convective device respectively, wherein the hose connector and the two output connectors are in fluid connection.

Item C32. A tubular convective system, comprises:
a tubular convective device comprising: a tubular structure comprising a flexible material, the tubular structure having two ends, and a plurality of apertures on the tubular structure; and
a hose manifold comprising: a hose connector configured to connect to a hose, two outlet connectors configured to connect to the two ends of the tubular structure respectively, wherein the hose connector and the two output connectors are in fluid connection.

The present invention should not be considered limited to the particular examples and embodiments described above, as such embodiments are described in detail to facilitate explanation of various aspects of the invention. Rather the present invention should be understood to cover all aspects of the invention, including various modifications, equivalent processes, and alternative devices falling within the spirit and scope of the invention as defined by the appended claims and their equivalents.

What is claimed is:

1. A convective system, comprising:
an inflatable convective device having a single pneumatic structure and two openings into single pneumatic structure, wherein at least part of the inflatable convective device is air permeable;
a hose manifold comprising:
a hose connector configured to connect to a hose,
two outlet connectors configured to connect to the two openings respectively,
wherein the hose connector and the two outlet connectors are in fluid connection,
wherein at least one of the two outlet connectors further comprises a flexible flap configured to prevent slipping.

2. The convective system of claim 1, wherein the two outlet connectors open toward generally opposite directions.

3. The convective system of claim 1, wherein the two outlet connectors are generally parallel and open toward generally same directions.

4. The convective system of claim 1, wherein the hose manifold further comprises an attachment element configured to attach to a fixture.

5. The convective system of claim 1, wherein at least one of the two outlet connectors is slanted.

6. The convective system of claim 1, wherein at least one of the two outlet connectors comprises a generally triangular opening.

7. The convective system of claim 1, wherein at least one of the two outlet connectors comprises a generally round opening.

8. The convective system of claim 1, wherein at least one of the two outlet connectors comprises an expandable element.

9. The convective system of claim 1, wherein the hose manifold is rigid.

10. The convective system of claim 1, wherein the inflatable convective device is a tubular convective device.

11. The convective system of claim 10, wherein the tubular convective device comprises a blown film and a plurality of apertures disposed on the blown film.

12. The convective system of claim 11, wherein the tubular convective device comprises a first portion and a second portion separated from the first portion longitudinally, and wherein the plurality of apertures are only disposed on the first portion of the tubular convective device.

13. The convective system of claim 1, wherein the inflatable convective device comprises: a flexible first layer and a flexible second layer joining the first layer by a seal around a common periphery to form the single pneumatic structure.

14. The convective system of claim 1, wherein the single pneumatic structure is continuous.

15. The convective system of claim 1, wherein the flexible flap is formed from a soft thermoplastic elastomer.

\* \* \* \* \*